(12) United States Patent
Arimura

(10) Patent No.: US 6,680,295 B1
(45) Date of Patent: *Jan. 20, 2004

(54) METHOD AND PHARMACEUTICAL COMPOSITION FOR PREVENTION AND TREATMENT OF BRAIN DAMAGE

(75) Inventor: Akira Arimura, New Orleans, LA (US)

(73) Assignee: The Administrators of the Tulane Educational Fund, New Orleans, LA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,500

(22) PCT Filed: Sep. 21, 1995

(86) PCT No.: PCT/US95/12057
§ 371 (c)(1),
(2), (4) Date: May 21, 1997

(87) PCT Pub. No.: WO96/09064
PCT Pub. Date: Mar. 28, 1996

(30) Foreign Application Priority Data

Sep. 22, 1994 (WO) .............................. PCT/US94/10752

(51) Int. Cl.$^7$ .............................................. A61K 35/16
(52) U.S. Cl. ............................. 514/12; 514/2; 530/324; 435/7.1; 435/7.21; 435/63.4
(58) Field of Search ......................... 514/12; 530/324; 435/7.1, 7.21, 68.4

(56) References Cited

U.S. PATENT DOCUMENTS

| | | | |
|---|---|---|---|
| 4,445,514 A | * 5/1984 | Osterholm | 606/363 |
| 5,128,242 A | 7/1992 | Arimura et al. | 435/7.21 |
| 5,208,320 A | 5/1993 | Kitada et al. | 530/324 |
| 5,326,860 A | * 7/1994 | Onda et al. | 530/324 |
| 5,344,644 A | * 9/1994 | Igari et al. | 424/85.1 |
| 5,358,934 A | * 10/1994 | Borovsky et al. | 514/17 |

FOREIGN PATENT DOCUMENTS

| | | | |
|---|---|---|---|
| EP | 511600 A2 | * | 4/1992 |
| JP | 6-228002 | | 8/1994 |
| JP | 6228002 | * | 8/1994 |

OTHER PUBLICATIONS

Arimura et al. Novel hypothalamic peptides stiulate adenylate cyclase of neurons and astrocytes, and prevent gp–120–induced neuronal cell death. *72$^{nd}$ Annual Meeting Endocrine Society*, Abstract #1261 (1990).

Arimura. Pituitary adenylate cyclase activating polypeptide (PACAP): discovery and current status of research. *Regulatory Peptides*. 37:287–303 (1992).

Banks et al. Passage of pituitary adenylate cyclase activating polypeptide$_{1-27}$ and pituitary adenylate cyclase activating polypeptide$_{1-38}$ across the blood–brain barrier. *J. Pharmacology and Experimental Therapeutics*. 267:690–696 (1993).

Uchida et al. Prevention of ischemia–induced death of hippocampal neurons by pituitary adenylate cyclase activating polypeptide. *Brain Research*. 736:280–286 (1996).

Arimura, et al., *Annals of the New York Academy of Scieces*, vol. 739, issued Oct. 31, 1994, "PACAP Functions as a Neurotrophic Factor", pp. 228–243.

* cited by examiner

*Primary Examiner*—Michael Borin
(74) *Attorney, Agent, or Firm*—Pennie & Edmonds LLP

(57) ABSTRACT

The present invention relates to methods and pharmaceutical preparations for treating or preventing neuronal cell damage in the brain and other tissues in mammals, comprising administering an effective amount of a PACAP, or an agonist, analog or derivative thereof having PACAP neurotrophic activity, in a pharmaceutically acceptable carrier, in a concentration which is effective for protection of neuronal nerve cells in vivo.

8 Claims, 12 Drawing Sheets

PACAP38:

His-Ser-Asp-Gly-Ile-Phe-Thr-Asp-Ser-Tyr-Ser-Arg-Tyr-Arg-Lys-Gln
Met-Ala-Val-Lys-Lys-Tyr-Leu-Ala-Ala-Val-Leu-Gly-Lys-Arg-Tyr-Lys-
Gln-Arg-Val-Lys-Asn-Lys-NH$_2$ (SEQ ID NO:1)

PACAP27

His-Ser-Asp-Gly-Ils-Phe-Thr-Asp-Ser-Tyr-Ser-Arg-Tyr-Arg-Lys-Gln-
Met-Ala-Val-Lys-Lys-Tyr-Leu-Ala-Ala-Val-Leu-NH$_2$ (SEQ ID NO:2)

FIG. I

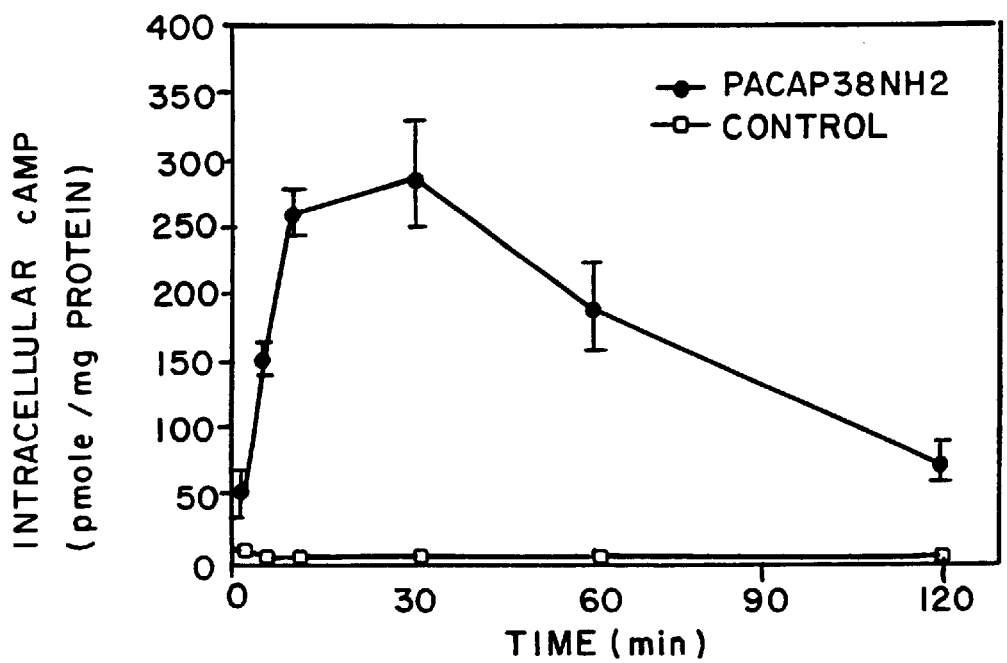
FIG. IIA
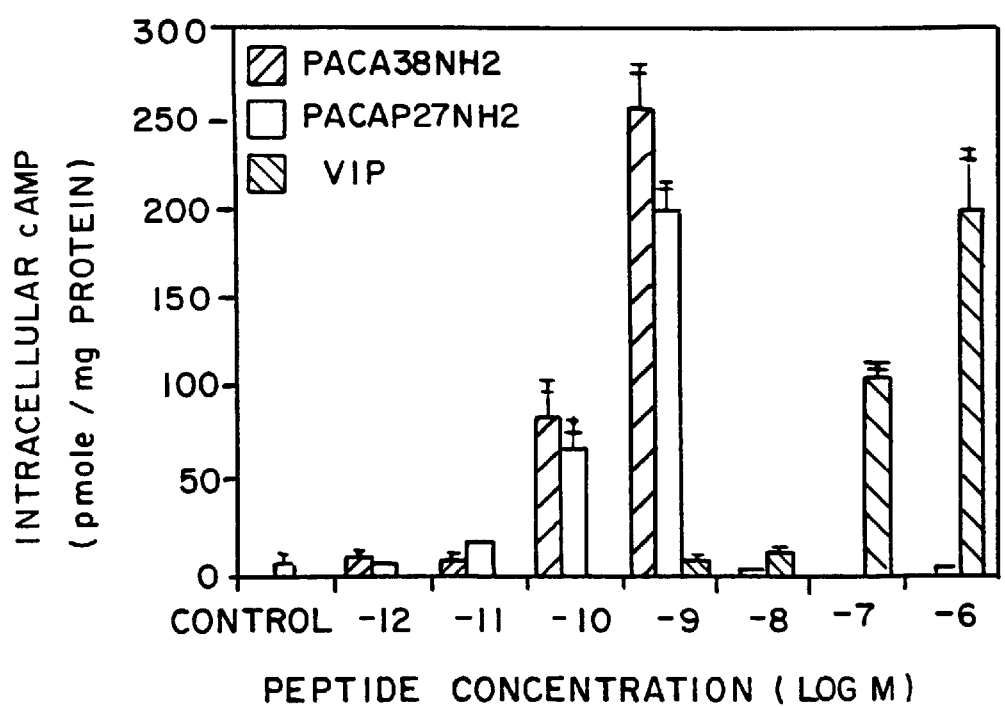
FIG. IIB

SEQUENCE LISTING

```
<160> NUMBER OF SEQ ID NOS: 26

<210> SEQ ID NO 1
<211> LENGTH: 38
<212> TYPE: PRT
<213> ORGANISM: Artificial
<220> FEATURE:
<223> OTHER INFORMATION: Description of Artificial Sequence: PACAP
<220> FEATURE:
<223> OTHER INFORMATION: The last amino acid in this peptide has a
      functional group of NH2

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Artificial
<220> FEATURE:
<223> OTHER INFORMATION: Description of Artificial Sequence: PACAP
<220> FEATURE:
<223> OTHER INFORMATION: The last amino acid in this peptide has a
      functional group of NH2

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 3
<211> LENGTH: 27
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 3

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25
```

```
<210> SEQ ID NO 4
<211> LENGTH: 27
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 4

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu
            20                  25

<210> SEQ ID NO 5
<211> LENGTH: 28
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 5

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly
            20                  25

<210> SEQ ID NO 6
<211> LENGTH: 28
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 6

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly
            20                  25

<210> SEQ ID NO 7
<211> LENGTH: 29
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
```

```
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 7

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys
            20                  25

<210> SEQ ID NO 8
<211> LENGTH: 29
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 8

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys
            20                  25

<210> SEQ ID NO 9
<211> LENGTH: 30
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 9

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg
            20                  25                  30

<210> SEQ ID NO 10
<211> LENGTH: 30
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 10

His Ser Asp Gly Ile Phe Thr Asp Ser Tyr Ser Arg Tyr Arg Lys Gln
1               5                   10                  15
```

```
Xaa Ala Val Lys Lys Tyr Leu Ala Ala Val Leu Gly Lys Arg
            20                  25                  30

<210> SEQ ID NO 11
<211> LENGTH: 31
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 11

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr
            20                  25                  30

<210> SEQ ID NO 12
<211> LENGTH: 31
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 12

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr
            20                  25                  30

<210> SEQ ID NO 13
<211> LENGTH: 32
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 13

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

<210> SEQ ID NO 14
<211> LENGTH: 32
<212> TYPE: PRT
<213> ORGANISM: Artificial
<220> FEATURE:
<223> OTHER INFORMATION: Description of Artificial Sequence: PACAP
```

```
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 14

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

<210> SEQ ID NO 15
<211> LENGTH: 33
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 15

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln

<210> SEQ ID NO 16
<211> LENGTH: 33
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 16

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln

<210> SEQ ID NO 17
<211> LENGTH: 34
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
``` functional group of NH2

<400> SEQUENCE: 17

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg

<210> SEQ ID NO 18
<211> LENGTH: 34
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 18

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg

<210> SEQ ID NO 19
<211> LENGTH: 35
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 19

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val
        35

<210> SEQ ID NO 20
<211> LENGTH: 35
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 20

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val
        35

<210> SEQ ID NO 21
<211> LENGTH: 36
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 21

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys
   35

<210> SEQ ID NO 22
<211> LENGTH: 36
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
functional group of OH

<400> SEQUENCE: 22

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys
        35

<210> SEQ ID NO 23
<211> LENGTH: 37
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 23

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn
        35

<210> SEQ ID NO 24
<211> LENGTH: 37
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 24

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn
        35

<210> SEQ ID NO 25
<211> LENGTH: 38
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of NH2

<400> SEQUENCE: 25

His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn Lys
        35

<210> SEQ ID NO 26
<211> LENGTH: 38
<212> TYPE: PRT
<213> ORGANISM: Artificial
<220> FEATURE:
<223> OTHER INFORMATION: Description of Artificial Sequence: PACAP
<220> FEATURE:
<221> NAME/KEY: SITE
<222> LOCATION: 17
<223> OTHER INFORMATION: Xaa = Met, Gly, Ser, Phe, Nle, Arg or Glu
<220> FEATURE:
<223> OTHER INFORMATION: The last amino acid in this peptide has a
      functional group of OH

<400> SEQUENCE: 26

-continued

```
His Ser Asp Gly Ile Phe Thr Asp Ser Tyr Ser Arg Tyr Arg Lys Gln
1               5                   10                  15

Xaa Ala Val Lys Lys Tyr Leu Ala Ala Val Leu Gly Lys Arg Tyr Lys
            20                  25                  30

Gln Arg Val Lys Asn Lys
            35
```

METHOD AND PHARMACEUTICAL COMPOSITION FOR PREVENTION AND TREATMENT OF BRAIN DAMAGE

This application Ser. No. 08/809,500 is a 371 of PCT/US95/12057 filed Sep. 21, 1995; which claims priority from the International Application No. PCT/US94/10752 filed Sep. 22, 1994.

This invention was supported in part by National Institutes of Health Grant DK 09094. The government has certain rights in this invention.

FIELD OF THE INVENTION

The present invention relates to a method for the prevention and treatment of neuronal cell damage in the brain of mammals, including, for example, damage induced by ischemia followed by reperfusion or that induced by toxic substances.

BACKGROUND OF THE INVENTION

Neuronal cell damage results from many causes. The most common cause of neuronal cell damage is ischemia/reperfusion of the brain following vascular occlusion by thrombosis or embolism, and cardiac failure, which occasionally occurs during heart surgery. Neuronal cell damage or death can be caused both by the ischemia and by reperfusion of blood after the transient ischemia has subsided. See W. D. Dietrich, "Morphological Manifestations of Reperfusion Injury in Brain," Ann. N.Y. Acad. Sci. 723:15 (1994). Transient ischemia of the brain sometimes also occurs in newborn babies during complicated deliveries. Neuronal cell damage or death can also be induced by various toxic substances, including, for example, the gp120 envelope glycoprotein of the HIV virus, other viral toxins, bacterial toxins, animal toxins, e.g., snake venom, toxic waste, e.g., methylated mercury, and others. The methods and compositions of the present invention can be used to protect and/or attenuate neuronal cells in the brain, spinal cord or elsewhere in the body, caused by trauma, infection e.g., encephalitis, AIDS or degenerative diseases such as Parkinson's disease, Alzheimer's disease, etc.

Brain cell damage frequently results in permanent impairment of brain function. Memory loss, emotional instability, impairment of speech, impairment of movement, recognition, learning, sight, hearing, sensation or other body functions are typical symptoms. At present, no effective method for prevention or treatment of brain cell damage in mammals is available.

Pituitary adenylate cyclase activating polypeptide (PACAP) was originally isolated from ovine hypothalamic tissues based on its ability to activate adenylate cyclase in rat pituitary cell cultures. A. Miyata, et al., *Biochem Biophys Res Commun* 164: 567–574 (1989). As published, PACAP exists in two basic forms: the complete form with 38 amino acids (PACAP38) and a truncated form with 27 amino acids (PACAP27). A. Miyata, A. et al., *Biochem Biophys Res Commun* 170: 643–648 (1990). The amino acid sequences for those two versions are shown in FIG. 1 (SEQ ID NO:1 and SEQ ID NO:2). PACAP is a new member of the secretin/glucagon/vasoactive intestinal peptide (VIP) family, being the most homologous to VIP, but its adenylate cyclase stimulating activity in cultured pituitary cells, neurons and astrocytes is about 1,000–10,000 times greater than VIP, A. Miyata et al., supra. PACAP is a pleiotropic neuropeptide, exhibiting a number of neurotropic actions in different organs and tissues. For example, PACAP enhances proliferation and differentiation of sympathetic neuroblasts, stimulates neurite outgrowth of an adrenal chromaffin cell line, PC12 cells, and stimulates growth of astrocytes, E. DiCicco-Bloom et al., *Reg. Pep.* 37: 219 (1992); Okazaki et al., *FEBS* 29F: 49–566 (1992). The in vivo cytoprotective action of PACAP has been investigated in rats with transient forebrain ischemia. Uchida et al., *Soc. Neurosci. Abst.,* Vol. 20, 1994 (Abstract No. 193.10).

There are two types of PACAP receptors (Gottschall et al., *Endocrinology* 127/1:272–277 (1990); Shivers et al., *Endocrinology,* 128/6:3055–3056 (1991); A. Arimura, Trends in Endocrinology and Metabolism, 3/8: 288–294 (1992). The Type I PACAP receptor specifically binds to PACAP with high affinity, but do not bind to VIP. The Type II PACAP receptors bind to both PACAP and VIP with similar high affinities, and may be very similar to or identical with the VIP receptor.

SUMMARY OF THE INVENTION

The present invention relates to a method and pharmaceutical preparations for treating or preventing neuronal cell damage in mammals, comprising administering a effective amount of a PACAP, or an agonist, analog or derivative thereof having PACAP neurotrophic activity, in a pharmaceutically acceptable carrier, in a concentration which is effective for protection of neuronal nerve cells in vivo.

It has now been discovered that, unexpectedly, although PACAP is extremely effective in protecting and/or resuscitating neuronal cells, there is a rather narrow window of concentrations of PACAP which provide such results, i.e., the effectiveness of the treatment falls off rapidly both above and below that concentration range. Thus the present invention involves a method of treatment of mammalian neuronal cells in which the concentration of the PACAP compound is between about $10^{-15}$ and $10^{-12}$ M in the tissues. Even more unexpectedly, it has been discovered that within the generally effective concentration range of the PACAP pharmaceuticals of this invention, there are two sub ranges of concentration, in each of which there is a peak effectiveness, above and below which the effectiveness of the composition falls off to a significant degree. As shown in FIG. 8, the preferred concentration range for treatment with the PACAP compounds of the present invention lies between about $10^{-14}$ and about $10^{-12}$ M and another range of concentration lies between about $10^{-11}$ and about $10^{-9}$ M. The preferred concentration range for treatment is the range between about $10^{-14}$ and about $10^{-12}$ M in the tissue, which permits treatment of the subject with minimal risks of side effects from the treatment. The present discovery makes possible the use of such PACAP pharmaceuticals in extremely low concentrations to provide very substantial protection of neuronal cells, such as brain cells, from death due to transient ischemia, reperfusion, toxic substances, trauma, or other causes.

Pharmaceutical compositions in accordance with the present invention include PACAP, in either of its forms, commonly referred to as PACAP38 and PACAP27, as well as any peptide or non-peptide agonist for PACAP receptors, especially agonists for the Type I PACAP receptor. Preferably the PACAP compound is a polypeptide, or a salt or derivative thereof, which contains at least twelve amino acids joined in a sequence corresponding to a part of the sequence shown for PACAP38 in FIG. 1, and which binds to at least one receptor which binds to PACAP. As used herein a "$PACAP_{12}$ agonist" refers to a polypeptide, or salt or derivative thereof, which has at least 12 amino acids corresponding in sequence to some part of the amino acid sequence of PACAP38, as shown in FIG. 1, and which binds to at least one PACAP receptor. Similarly, the terms "PACAP$_{23}$ agonist" and "PACAP$_{27}$ agonist" refer to polypeptides, or salts or derivatives thereof, which has at least 23 and 27 amino acids, respectively, corresponding in sequence to some part of the amino acid sequence of PACAP38, as shown in FIG. 1, and which binds to at least one PACAP receptor. Determination of the amino acid sequence of the polypeptide, and determination as to whether it binds to a PACAP receptor, are both well within the skill in the art. The ability to treat neuronal cells at such low concentrations also makes possible the administration of the PACAP compounds intravenously or otherwise into the blood, in concentrations sufficient to provide PACAP compound transfers across the blood/brain barrier sufficient to provide concentrations of the PACAP compound in contact with the neuronal cells which are effective to protect and/or resuscitate the traumatized neuronal cells.

It has also been discovered that administration of the PACAP compound is effective in protecting and/or resuscitating traumatized neuron cells up to at least 24 hours after injury.

Preferably the PACAP compound has the general formula:

$$X\text{-}PACAP_{[a-b]}\text{-}Y$$

wherein X is H or a solubility effecting group such as $C_{1-20}$ carboxylic acid moiety, such as formyl, acetyl, etc.; a and b are N and C terminus amino acids taken in the sequence of PACAP38 as shown in FIG. 1, and Y is H, $NH_2$, OH, or $C_{1-4}$ carboxy. For adjustment of lipophilic nature to increase the amount of PACAP compound passing the blood/brain barrier, it is preferred that X is a fatty acid moiety, preferably derived from Lauric, Myristic, Palmitic, Stearic, or Oleic acid, most preferably from Palmitic or Stearic acid. Thus expressed, PACAP38 is PACAP$_{[1-38]}$-NH$_2$, i.e., X is H, Y is the $NH_2$ attached to the C-terminal Lysine, and the compound has the complete sequence of 1–38 amino acids of FIG. 1. The polypeptide can be substituted at either end with moieties which favorably effect the solubility in the carrier, or favorably effect the ability of the PACAP compound to transfer across the blood brain barrier without substantially adversely effecting the effectiveness of the compound. Thus X can be an organic acid or salt thereof, preferably containing only alkyl groups of $C_{1-25}$, preferably $C_{1-20}$, or a residue from such an acid, e.g., an ether derived from such an acid. Low molecular weight ($C_{1-4}$) acids or acid residues can be used to increase the solubility of the polypeptide in the pharmaceutical composition, or in bodily fluids. Larger molecular weight moieties, such as the $C_{12-20}$ long chain fatty acid residues, can be used to enhance the transferability of the PACAP compound across the blood brain/barrier. Substituents at the C-terminus of the polypeptide can also be used to enhance the solubility of the PACAP compound without deleteriously effecting its usefulness. For example, the amino ($NH_2$) group on the C-terminal amino acid can be substituted by a hydroxyl group or a lower ($C_{1-4}$) alcohol or carboxyl group.

It is also possible to make various substitutions of certain of the amino acids in the PACAP sequence, to make minor adjustments in the physical properties of the molecule without substantially effecting its usefulness in treatment of neuronal cells. For example, substitution of less reactive amino acids can provide increased stability and shelf life of the pharmaceutical composition. Thus it is possible to make one or more of the following substitutions:

| Location | Substitute (s) |
|---|---|
| For His at position 1 | Tyr, Ala, Arg or Glu |
| For Asp at position 3 | Glu |
| For Gly at position 4 | Ala |
| For Asp at position 8 | Glu |
| For Ser at position 9 | Asn |
| For Ser at position 11 | Thr |
| For Tyr at position 13 | Leu |
| For Met at position 17 | Gly, Ser, Phe, Nle, Arg or Glu |
| For Ala at positions 24, 25 | Ser |

As used in the present application, such substitutions will be referred to in brackets prior to the modified PACAP structure. For example, [Glu$^{3,8}$]PACAP$_{[1-27]}$-NH$_2$ refer to PACAP27 wherein the asparagine at position 3 and the asparagine at position 8 have each been replaced by glutamic acid.

Suitable exemplary compositions are disclosed below.

The most preferred active ingredient of the pharmaceutical composition is PACAP 38, its salts and derivatives. The next most preferred is PACAP27, its salts and derivatives. As used herein, "PACAP27" and "PACAP38" refer to the polypeptides which have the same amino acid sequence as amino acids 1–27 and 1–38, respectively, of PACAP38, as shown in FIG. 1. Thus both PACAP38 and PACAP27 come with the scope of the terms "PACAP$_{12}$" "PACAP$_{23}$" and "PACAP$_{27}$." Other suitable PACAP type compounds include:

1. N$^\alpha$Acetyl-PACAP$_{1-38}$-NH$_2$
   where PACAP$_{1-38}$ represents amino acids 1–38 of SEQ ID NO:1.
2. N$^\alpha$Acetyl-PACAP$_{2-38}$-NH$_2$
   where PACAP$_{2-38}$ represents amino acids 2–38 of SEQ ID NO:1.
3. N$^\alpha$-Stearyl-PACAP$_{1-38}$-NH$_2$
   where PACAP$_{1-38}$ represents amino acids 1–38 of SEQ ID NO:1.
4. N$^\alpha$-Stearyl-PACAP$_{2-38}$-NH$_2$
   where PACAP$_{2-38}$ represents amino acids 2–38 of SEQ ID NO:1.
5. PACAP$_{1-38}$-OH
   where PACAP$_{1-38}$ represents amino acids 1–38 of SEQ ID NO:1.
6. PACAP$_{1-30}$-NH$_2$
   where PACAP$_{1-30}$ represents amino acids 1–30 of SEQ ID NO:1.
7. PACAP$_{2-30}$-NH$_2$
   where PACAP$_{2-30}$ represents amino acids 2–30 of SEQ ID NO:1.
8. N$^\alpha$-Acetyl-PACAP$_{2-30}$-NH$_2$
   where PACAP$_{2-30}$ represents amino acids 2–30 of SEQ ID NO:1.
9. PACAP$_{1-27}$-NH$_2$
   where PACAP$_{1-27}$ represents amino acids 1–27 of SEQ ID NO:1 or SEQ ID NO:2.
10. N$^\alpha$-Acetyl-PACAP$_{1-27}$-NH$_2$
    where PACAP$_{1-27}$ represents amino acids 1–27 of SEQ ID NO:1 or SEQ ID NO:2.
11. N$^\alpha$-Acetyl-PACAP$_{2-27}$-NH$_2$
    where PACAP$_{2-27}$ represents amino acids 2–27 of SEQ ID NO:1 or SEQ ID NO:2.
12. N$^\alpha$-Stearyl-PACAP$_{1-27}$-NH$_2$
    where PACAP$_{1-27}$ represents amino acids 1–27 of SEQ ID NO:1 or SEQ ID NO:2.
13. N$^\alpha$-Stearyl-PACAP$_{2-27}$-NH$_2$
    where PACAP$_{2-27}$ represents amino acids 2–27 of SEQ ID NO:1 or SEQ ID NO:2.

-continued

14. PACAP$_{2-27}$-NH$_2$
    where PACAP$_{2-27}$ represents amino acids
    2–27 of SEQ ID NO:1 or SEQ ID NO:2.
15. [Tyr$^1$]PACAP$_{1-b}$-NH$_2$, b = 27–38
    where PACAP$_{1-b}$ represents amino acids
    1–b of SEQ ID NO:1, where b represents
    amino acids 27 to 38.
16. [Ala$_1$]PACAP$_{1-b}$-NH$_2$, b = 27–38
    where PACAP$_{1-b}$ represents amino acids
    1–b of SEQ ID NO:1, where b represents
    amino acids 27 to 38.
17. [Arg$^1$]PACAP$_{1-b}$-NH$_2$, b = 27–38
    where PACAP$_{1-b}$ represents amino acids
    1–b of SEQ ID NO:1, where b represents
    amino acids 27 to 38.
18. [Glu$^1$]PACAP$_{1-b}$-NH$_2$, b = 27–38
    where PACAP$_{1-b}$ represents amino acids
    1–b of SEQ ID NO:1, where b represents
    amino acids 27 to 38.
19. [Glu$^3$]PACAP$_{1-b}$-NH$_2$, b = 27–38
    where PACAP$_{1-b}$ represents amino acids
    1–b of SEQ ID NO:1, where b represents
    amino acids 27 to 38.
20. [Glu$^8$]PACAP$_{1-b}$-NH$_2$, b = 27–38
    where PACAP$_{1-b}$ represents amino acids
    1–b of SEQ ID NO:1, where b represents
    amino acids 27 to 38.
21. [Glu$^{3,8}$]PACAP$_{1-b}$-NH$_2$, b = 27–38
    where PACAP$_{1-b}$ represents amino acids
    1–b of SEQ ID NO:1, where b represents
    amino acids 27 to 38.
22. [Asn$^9$]PACAP$_{1-b}$-NH$_2$, b = 27–38
    where PACAP$_{1-b}$ represents amino acids
    1–b of SEQ ID NO:1, where b represents
    amino acids 27 to 38.
23. [Thr$^{11}$]PACAP$_{1-b}$-NH$_2$, b = 27–38
    where PACAP$_{1-b}$ represents amino acids
    1–b of SEQ ID NO:1, where b represents
    amino acids 27 to 38.
24. [Leu$^{13}$]PACAP$_{1-b}$-NH$_2$, b = 27–38
    where PACAP$_{1-b}$ represents amino acids
    1–b of SEQ ID NO:1, where b represents
    amino acids 27 to 38.
25. [Ser$^{24,25}$]PACAP$_{1-b}$-NH$_2$, b = 27–38
    where PACAP$_{1-b}$ represents amino acids
    1–b of SEQ ID NO:1, where b represents
    amino acids 27 to 38.
26. X-[Gly$^{17}$]PACAP$_{1-b}$-NH$_2$, X = C$_{10-18}$
    fatty acid; b = 27–38
    where PACAP$_{1-b}$ represents amino acids
    1–b of SEQ ID NO:1, where b represents
    amino acids 27 to 38.
27. X-[Ser$^{17}$]PACAP27-NH$_2$, X = C$_{10-18}$ fatty acid;
28. X-[Phe$^{17}$]PACAP27-NH$_2$, X = C$_{10-18}$ fatty acid;
29. X-[Glu$^{17}$]PACAP27-NH$_2$, X = C$_{10-18}$ fatty acid;
30. X-[Arg$^{17}$]PACAP27-NH$_2$, X = C$_{10-18}$ fatty acid;
31. X-[Nle$^{17}$]PACAP27-NH$_2$, X = C$_{10-18}$ fatty acid;
32. X-[Ala$^4$]PACAP(1–23)-NH$_2$, X = C$_{10-18}$ fatty acid;
33. [Ala$^4$, Leu$^{13}$]PACAP$_{1-b}$-NH$_2$, b = 23–38
    where PACAP$_{1-b}$ represents amino acids
    1–b of SEQ ID NO:1, where b represents
    amino acids 23 to 38.
34. [Leu$^{13}$]PACAP$_{1-b}$-NH$_2$, b = 23–38
    where PACAP$_{1-b}$ represents amino acids
    1–b of SEQ ID NO:1, where b represents
    amino acids 23 to 38.
35. [Tyr$^1$]PACAP$_{1-b}$-NH$_2$, b = 23–26
    where PACAP$_{1-b}$ represents amino acids
    1–b of SEQ ID NO:1 or SEQ ID NO:2, where b represents
    amino acids 23 to 26.
36. PACAP$_{1-b}$-NH$_2$, b = 23–26
    where PACAP$_{1-b}$ represents amino acids
    1–b of SEQ ID NO:1 or SEQ ID NO:2, where b represents
    amino acids 23 to 26.
37. PACAP$_{1-24}$-NH$_2$
    where PACAP$_{1-24}$ represents amino acids
    1–24 of SEQ ID NO:1 or SEQ ID NO:2.
38. PACAP$_{1-23}$-OH
    where PACAP$_{1-23}$ represents amino acids
    1–23 of SEQ ID NO:1 or SEQ ID NO:2.
39. PACAP$_{2-23}$-NH$_2$
    where PACAP$_{2-23}$ represents amino acids
    2–23 of SEQ ID NO:1 or SEQ ID NO:2.
40. N$^\alpha$-X-PACAP$_{1-38}$-NH$_2$, X = C$_{10-18}$ fatty acid
    where PACAP$_{1-38}$ represents amino acids
    1–38 of SEQ ID NO:1.
41. N$^\alpha$-X-PACAP$_{2-38}$-NH$_2$, X = C$_{10-18}$ fatty acid
    where PACAP$_{2-38}$ represents amino acids
    2–38 of SEQ ID NO:1.
42. N$^\alpha$-X-PACAP$_{1-27}$-NH$_2$, X = C$_{10-18}$ fatty acid
    where PACAP$_{1-27}$ represents amino acids
    1–27 of SEQ ID NO:2.
43. N$^\alpha$-X-PACAP$_{2-27}$-NH$_2$, X = C$_{10-18}$ fatty acid
    where PACAP$_{2-27}$ represents amino acids
    2–27 of SEQ ID NO:2.
45. Any peptide or non-peptide agonist (except those listed above) for PACAP receptor 1 and organic and inorganic salts thereof.

BRIEF DESCRIPTION OF THE DRAWINGS

FIG. 1. shows the primary structure PACAP38 (SEQ ID NO:1) and PACAP27 (SEQ ID NO:2).

FIG. 10A shows temporal pattern of intracellular cAMP concentrations after addition of 10$^{-9}$ M PACAP38. FIG. 10B shows the mean of intracellular cAMP concentrations determined 10 min after addition of varying doses of PACAP38, PACAP27 or VIP. *indicates level of significance, P<0.05.

FIGS. 11A and 11B are graphs showing cAMP response of cultured rat astrocytes to PACAP. Astrocytes cultures were prepared from brain of neonatal rats. Astrocytes were allowed to proliferate for 7–10 days before experiments. FIG. 11A shows temporal pattern of intracellular cAMP concentrations after addition of 10$^{-9}$ M PACAP38. FIG. 11B shows the mean of intracellular cAMP concentrations determined 10 min after addition of varying doses of PACAP38, PACAP27 or VIP. *indicates level of significance, P<0.05. Other experimental protocols are same as shown in FIG. 10.

DETAILED DESCRIPTION OF THE INVENTION

Figure 2:
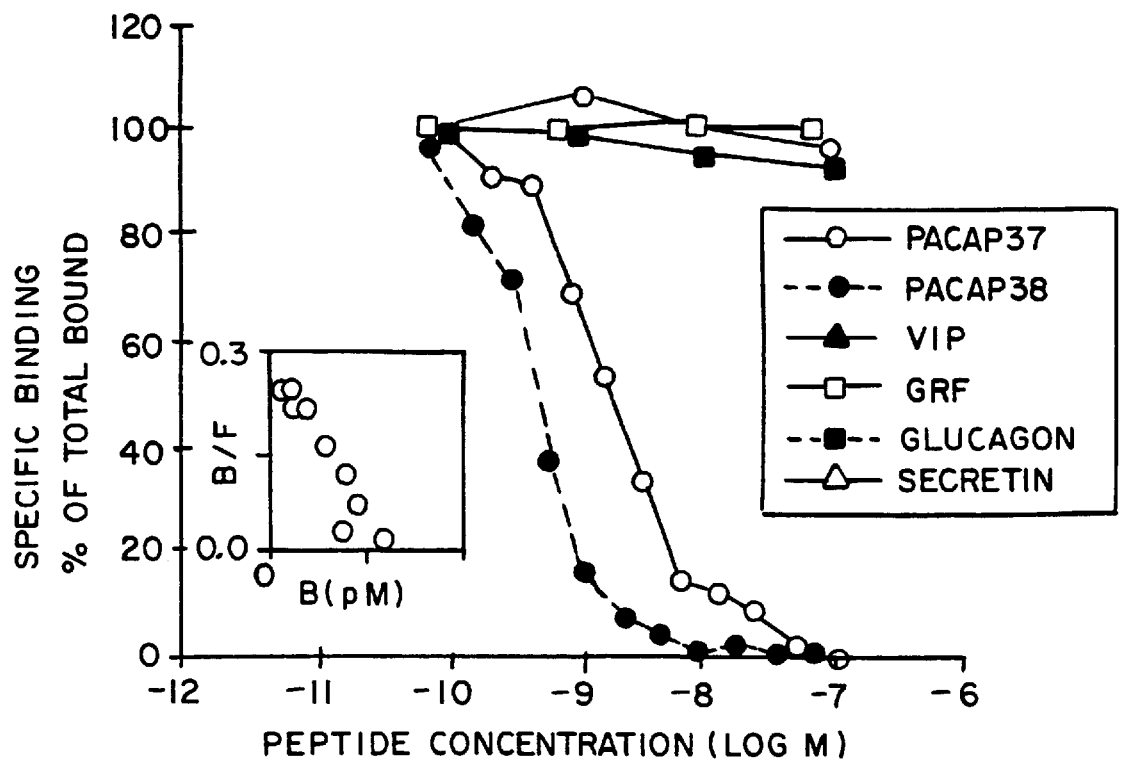
FIG. 2. is a representative displacement curve of [$^{125}$I] PACAP27 binding to rat brain membrane preparations by PACAP and structurally related peptides. Inset shows Scatchard plot analysis of the data from [$^{125}$I]PACAP27 binding displaced by unlabeled PACAP27.

It has now been discovered that sustained intracerebroventricular administration of PACAP can be used to protect neuronal cells and significantly prevent neuronal cell damage and death induced by ischemia, hemorrhage, trauma, toxic substances or other causes. It is particularly effective in treating neuronal cell damage caused by transient ischemia followed by reperfusion. Unexpectedly, the present inventors found that PACAP compounds are most effective in vivo in a particular concentration range, above which the effectiveness drops off. Most surprisingly, within that effective range, there are sub ranges of concentration, within which the effectiveness peaks and drops off, and the activity of the PACAP compound in the lower sub range is higher than at higher concentrations, thus permitting use of the PACAP compounds at extremely low concentrations, in turn avoiding possible side effects and complications.

Accordingly, the present invention provides a method for the treatment and prevention of neuronal cell damage and death, preferably brain cell damage and death, in vitro and/or in vivo, induced by various causes comprising administrating to neuronal cells or to a mammal in need thereof an effective amount of a PACAP or an agonist thereof, which interacts with specific Type I PACAP receptors. Preferably, the in vivo mode of administration is intraventricular or intravenous.

While not wishing to be bound by theory, the neurotrophic action of PACAP appears to take place at two different sites. PACAP-stimulates proliferation of sympathetic neuroblast and neurite outgrowth in PC12 cells directly, but it requires nanomolar concentration. Cytoprotective action of PACAP on chick embryos also requires nanomolar concentration of the peptide, much higher than the effective concentrations discovered in connection with the present invention. That type of cytoprotective action is believed to be mediated via or through adenylate cyclase activation by PACAP.

Applicant has also shown that when neuronal cells are plated on a feeder layer of astrocytes, addition of HIV envelope glycoprotein gp120 results in significant cell death. Yet, when small concentration of PACAP, e.g., $10^{-13}$M, was added to the culture, the gp120-induced neuronal cell death was completely prevented. In such cases, higher concentrations of PACAP have been shown to be less effective. Since this cytoprotective action is difficult to demonstrate in neuron cultures in the absence of astrocytes, this cytoprotective action is considered to be mediated through astrocytes, which express an extremely high affinity Type I PACAP receptors. PACAP at such a low concentration does not stimulate adenylate cyclase or phospholipase C, and as a result, the cytoprotective action may be mediated by one or more other second messengers, most likely by alteration of intracellular $Ca^{2+}$. PACAP which has been found to increase intracellular $Ca^{2+}$ of cultured pancreatic beta cells at $10^{-13}$M (Yada et al., *J. Biol. Chem.*, in press 1994). Based on this evidence it is believed that a subtype of Type I PACAP receptors with an extremely high affinity may be expressed on astrocytes in vivo under certain conditions, such as ischemia-induced brain injury. As discussed above, astrocytes with Type I PACAP receptors begin appearing 2 days after ischemia and the number increases over 7 days after ischemia. Applicants' in vitro examination of gp120-induced brain cell death suggests that the interaction of PACAP with these newly expressed receptors in astrocytes may stimulate synthesis and release of a neurosurvival factor that prevents neuronal cell death.

In accordance with the method of the present invention, PACAP may be used in the treatment and prevention of neuronal cell damage resulting from ischemia/reperfusion, trauma, hemorrhage, infection and exposure to toxic substances. PACAP can also be used for 1) treatment of congestive heart failure of neonate, through its inotropic action and stimulation of adrenalin secretion in vivo; 2) treatment of neuropathy, such as diabetic neuropathy; 3) treatment of spinal cord injury; 4) treatment of ischemia/reperfusion induced lung injury (cAMP has been shown to prevent such injury, and PACAP is a potent stimulater for cAMP production); 5) treatment of ischemia/reperfusion induced cardiac injury; 6) treatment of gastric and intestinal ulcer (PACAP regulates production of various growth factors which are known to prevent ulcer); 7) stimulation of neonatal and prenatal brain development; 8) protection of transplanted neural cells in the brain; 9) treatment of certain male infertility; 10) improvement of brain circulation; 11) treatment of shock, such as the condition resulting from exposure to bacteria toxin.

Mammalian subjects which can be treated with the PACAP compounds and compositions in accordance with the present invention include, for example, cattle, swine, sheep, monkeys, dogs, cats, rodents, such as laboratory animals, and humans. Further, PACAP stimulates growth and differentiation of neuronal and glial cells and cell lines in vitro. Any cell line which possesses PACAP receptors can be stimulated by PACAP in growth and differentiation.

Synthesis of PACAP38, PACAP27 and their related peptides.

PACAP38, PACAP27, PACAP their agonist analogs, precursors and salts are prepared in a manner which will be apparent to the skilled in the art. The peptides were synthesized by solid phase techniques using an automated peptide synthesizer (Beckman 990B). 4-methyl benzhydrylamine resin and PAM-resin were employed for the synthese of C-terminal amide form peptides and C-terminal free form peptides, respectively. The peptide chain was elongated on the resin with the use of $N^\alpha$-Boc-amino acid derivatives such as:

Boc-Lys(Cl-Z)-OH, Boc-Asn-OH, Boc-Val-OH, Boc-Arg(Tos)-OH, Boc-Gin-OH, Boc-Tyr(Br-Z)-OH, Boc-Leu-OH, Boc-Ala-OH, Boc-Met-OH, Boc-Ser(Bzl)-OH, Boc-Asp(OBzl)-OH, Boc-Thr(Bzl)-OH, Boc-Phe-OH, Boc-Ile-OH, Boc-His(Tos)-OH, Boc-Glu(OBzl)-OH and Boc-Nle-OH These $N^\alpha$Boc amino acid derivatives were successively introduced to the peptide chain in the presence of diisopropylcarbodiimide in dichloromethane with the exception of Boc-Asn-OH and Boc-Glyn-OH which were coupled in the presence of 1-hydroxybenzotriazole as a catalyst in DMF. The completed, protected peptide resins (90.025 mmol each) were treated with 20 mL of anhydrous hydrogen fluoride containing 10% anisole and 100 mg of dithiothreitol for 45 min at 0° C. After removal of the hydrogen fluoride under a stream of nitrogen, the free peptides were precipitated with either ether or ethyl acetate, filtered, and extracted with 2M AcOH. After lyophilization, the crude peptides were obtained. The crude peptides were purified by gel filtration on a column of SEPHADEX G-50 fine (2.5×100 cm) using 2M AcOH containing 0.02% β-mercaptoethanol as an eluent, followed by preparative reverse phase HPLC column (1.5×50 cm) of Vydac C-18 silica (15–20 mm particle size), which was eluted with a linear gradient of 10–35% acetonitrile in 0.1 % TFA at a flow rate of 3 mL/min.

The purity of each purified material was confirmed by analytical reverse phase HPLC, amino acid analyses, sequencing and FABMS.

Further information on preparation of the materials referred to in this application is disclosed, for example, in U.S. Pat. Nos. 5,198,542, 5,128,242, A. Sakiyama et al., *Pep. Chem.* 1991:215 (1991), and C. Kitada et al., *Pep. Chem.* 1990:239 (1991), the disclosures of which are hereby incorporated by reference.

PACAP or its agonists may be intracerebroventricularly administrated to a host in need thereof utilizing a variety of means known to the skilled artisan including, for example, an infusion system such as The SynchromMed Infusion System with Catheter Access Port (Medtronic Neurological, Minneapolis, Minn.). Suitable compositions for direct administration to the brain include the polypeptide in a carrier such as spinal fluid, artificial spinal fluid, or a combination of physiological saline, Ringer's solution, glucose (e.g., 3–7%, preferably about 5% by weight), and an isotonic phosphate buffer (pH of about 7). Artificial cerebrospinal fluid, comprises about 128 mM NaCl, 2.6 mM KCl, 1.3 mM $CaCl_2$, 20 mM $NaHCO_3$, 1.3 mM $Na_2HPO4$, pH 7.35 and contains 0.1% bovine serum albumin. For iv infusion 0.9% saline containing 0.1% bovine serum albumin may be used. Bovine serum albumin is used for protection of loss of the peptide due to adsorption. Bovine serum albumin can be replaced by any other inert protein such as human serum albumin and gelatin.

The amount of PACAP compound to be administered is sufficient to achieve a concentration in the tissue to be treated of from about $10^{-15}$ to about $10^{-12}$ M, more preferably from about $10^{-14}$ to about $10^{-12}$ M. In in vivo studies on laboratory rats, it was found that $10^{-13}$ M was achieved and maintained by intracerebroventricular ("icv")infusion of about 16 ng/kg body weight/hour for seven days. Thus the dosage ranges corresponding to the above concentration ranges are from about 0.16 ng/kg body weight/hour to 160 ng/kg body weight/hour, preferably either from 1.6 ng/kg body weight/hour to 160 ng/kg body weight/hour. Thus for a 300 g. rat, the optimal dosage for icv infusion was about 1 pmol/µl/hr for a seven day course of treatment, which is equal to a rate of 3.33 pmol (15.7 ng)/3.33 µl/kg/h. In a human patient weighing 70 kg, the infusion rate is about 233 pmol (1.1 µg)/233 µl/h. Thus, when an infusion rate of 233 µl/h is used the concentration of PACAP is 1 nmol/ml (4.5 µg/ml) for icv infusion. An infusion system, such as a SynchroMed Infusion System can deliver solution at a range between 4 µl and 900 µl/h. An infusion rate of 50–500 µl/h is preferred. Suitable concentrations of the PACAP compound in the pharmaceutically acceptable carrier for icv infusion are prepared according to the infusion rate. For example, when one wishes to infuse 1.1 µg/hour and an infusion rate of 50 µl/h is chosen, the concentration of PACAP is 1.1 µg/50 µl or 22 µg/ml. When 500 µl/h is chosen, a 2.2 µg/ml solution is prepared. Accordingly, suitable concentrations of the PACAP compound in pharmaceutically acceptable carrier for icv infusion at a rate of 1.1 µg/hour are from about 1.2 µg/ml to about 300 µg/ml, preferably from about 2.2 µg/ml to about 22 µg/ml. Suitable concentration ranges for other infusion rates can be likewise calculated.

As shown in Example 7, PACAP administered icv is not evenly distributed throughout the brain tissues. For example, administration of $^{125}$I labelled PACAP into the right lateral ventricle resulted in four times greater CPM in the right hippocampus than in the left. Thus, in order to achieve the desired concentration of PACAP in a specific brain tissue or region (e.g., left or right side), the amount of PACAP administered must be adjusted accordingly.

The administration of PACAP is not limited to the intracerebroventricular route. Despite the existence of blood-brain-barrier, a small portion of intravenously administered PACAP is transported into the brain. Banks, et al., *Journal of Pharmacology and Experimental Therapeutics*, 267: No. 2 690–696 (1993). PACAP38 is transported into the brain in a saturated manner. Therefore, it is also possible to administer PACAP and its analogs by a prolonged intravenous or even subcutaneous infusion to attain the optimal concentration of PACAP in the brain tissues for attaining the similar cytoprotective effect. The percentage of the amount of circulating PACAP which enters into the brain can be precisely calculated. Banks et al., supra. Analogs of PACAP with a greater lipophilic nature, such as PACAP analogs with fatty acid residue at the N-terminus, for example: $N^{\alpha}$-stearyl-[Nle$^{17}$]PACAP$_{1-38}$-NH$_2$ or $N^{\alpha}$-stearyl-[Nle$^{17}$]PACAP$_{2-38}$-NH$_2$ may be more preferable for such modes of administration.

Compositions for intravenous administration are preferably prepared by forming a solution of the PACAP compound in a water-soluble solvent (e.g. physiological saline, Ringer's solution). In tests with laboratory rats, it was determined that in order to achieve a concentration of $10^{-13}$ M in the brain, it was necessary to inject into the bloodstream about 1.7 pmol/h (or 7.7 ng per hour) of PACAP compound. This dose corresponds to 25.5 ng/kg/h. Thus, the dosage ranges corresponding to the above concentration ranges from about 0.25 ng/kg body weight/hour to 25 µg/kg body weight/hour, preferably from 0.25 ng/kg body weight/hour to about 2.5 µg/kg body weight/hour, most preferably from about 2.5 ng/kg body weight/hour to about 250 ng/kg body weight/hour. Based on the above a human patient weighing 70 kg, the optimal IV dose would be about 1.8 µg/h. Using an ordinary infusion pump, solution can be infused at, for example, 100 µl/h, and thus, 1.8 µg PACAP is dissolved in 100 µl to make 18 µg/ml in 0.9% saline, 5% glucose solution or a solution for IV infusion which contains various salts (these solutions are commercially available and used to meet patients' conditions.) Infusion rates can be modified to a rate faster or slower than 100 µl/h, and the concentrations of PACAP should be adjusted accordingly. For example, when the infusion rate is 1000 µl/h, the concentration of PACAP is 1.8 µg/ml.

The amount of PACAP in a pharmaceutical composition for intravenous administration is 10 to 100,000 times the amount that is effective at the active region, preferably 100 to 10,000 times and most preferably 500 to 5,000 times.

As desired, additives such as a dissolution aid (e.g.sodium salicylate, sodium acetate), buffer (e.g. sodium citrate, glycerine), isotonizing agent (e.g. glucose, invert sugar), stabilizer (e.g. human serum albumin, polyethylene glycol), preservatives (e.g. benzyl alcohol, phenol), or analgesics (e.g. benzalkonium chloride, procaine hydrochloride).

Compositions for administration of PACAP include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes and may be prepared by any methods well known in the art of pharmacy.

Such methods include the step of bringing into association the ingredients to be administered with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

The amount of PACAP in a composition for parenteral administration (e.g., suppository, sublingual tablet, nasal application) is 100 to 1,0000,000 times, the amount that is effective at the active region, preferably 1,000 to 100,000 times and most preferably 5,000 to 50,000 times.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing water. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration to the skin may be presented as ointments, creams, gels and pastes comprising the compound and a pharmaceutically acceptable carrier. A suitable topical delivery system is a transdermal patch containing the ingredient to be administered.

Sublingual tablets can be prepared by using binders (e.g. hydroxypropylcellulose, hydroxypropylmethylcellulose, polyethylene glycol), disintegrating agent (e.g. starch, carboxymethylcellulose calcium,), lubricant (e.g. magnesium stearate, talc)

Compositions suitable for rectal administration may be presented as a suppository with a suitable base comprising, for example, polyethylene glycol 600, cocoa butter or a salicylate.

Compositions suitable for nasal administration wherein the carrier is a solid include a coarse powder having a particle size, for example, in the range 20 to 500 microns. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tables of the kind previously described.

It should be understood that in addition to the ingredients particularly mentioned above, the formulations of this invention may include other agents conventional in the art having regard to the type of formulation in question, for example, those suitable for oral administration may include flavoring agents.

As the PACAP compound or an agonist for Type I PACAP receptor sites are extremely low in toxicity, compositions comprising these compounds are extremely low in toxicity.

The present invention is further illustrated by the following examples. These examples are provided to aid in the understanding of the invention and are not construed as a limitation thereof.

EXAMPLE 1

Ontogenetic Changes of PACAP and Its Receptors in the Rat Brain

Male CD rats (Charles River Breeding Labs., Wilmington, Mass.) were used throughout this example. The following regions of the brain were dissected at the indicated ages: embryonic day E14 (whole brain); E18 (whole brain, neocortex, hippocampus, and diencephalon); postnatal days P0, P7 and P14 (whole brain, neocortex, hippocampus, diencephalon, and cerebellum); and 1-, 2- and 3-months old (MO) (whole brain, neocortex, hippocampus, diencephalon, and cerebellum). After dissection, each region was immediately frozen on dry-ice and stored at −70 C. for up to 2 months until the receptor and peptide levels were determined. Each tissue was extracted and assayed for PACAP by RIA as described elsewhere. Arimura, et al., *Endocrinology* 129: 2787–2789 (1991). Specific binding sites in a membrane preparation of each tissue were determined by radioreceptor assay (RRA) using $^{125}$I-PACAP27 as the radiolabeled ligand as described previously. Gottschall, et al., *Endocrinology* 127: 272–277 (1990), and Gottschall, et al., *FASEB J* 5: 194–199 (1991).

Figure 3:
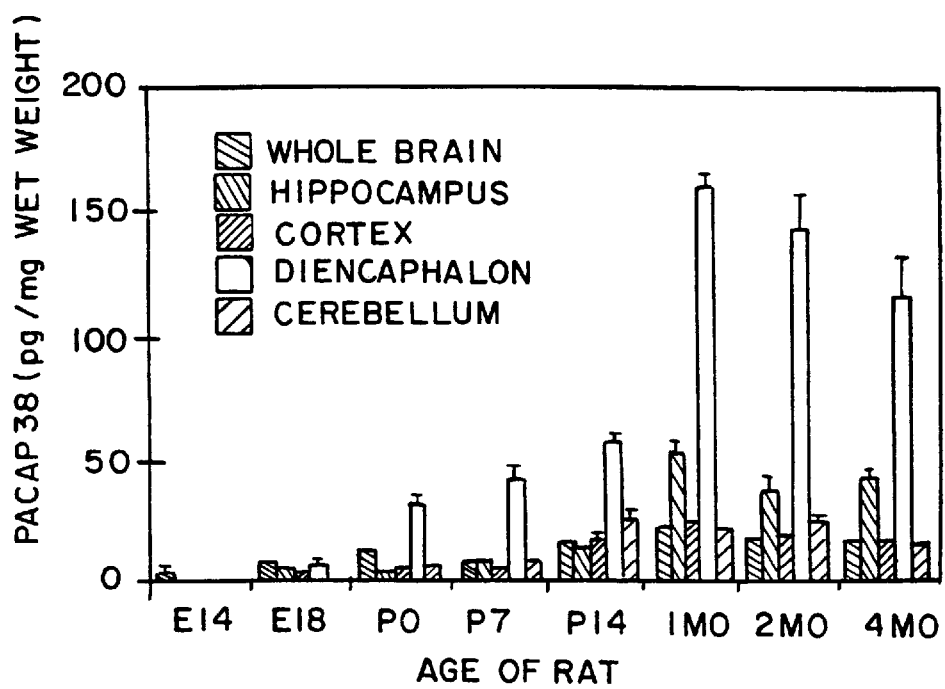
FIG. 3. is a Bmax for PACAP bindings sites in rat brains during development. PACAP binding sites were analyzed using both displacement curves of [$^{125}$I]PACAP27 binding by unlabeled PACAP27 and 38 simultaneously assuming that PACAP 27 and 38 share the same binding sites. The data are mean±SEM (n=3, except E18 (brain from rat embryo at embryonic day 18), where n=6).

The specific binding of $^{125}$I-PACAP27 to E18 brain membranes at 22C was rapid and reached equilibrium at 90 to 120 min. All equilibrium binding assays were thus performed at 22C for 90 min. The binding competition between $^{125}$I-PACAP27 and increasing concentrations of unlabeled PACAP 27 and other peptides are shown in FIG. 2. The maximal binding of 120 pM $^{125}$I-PACAP27 to 20 $\mu$g of membranes was approximately 23% of the tracer added. Scatchard analysis of the displacement off $^{125}$I-PACAP27 binding with unlabeled PACAP27 indicated the existence of a single class of binding sites (FIG. 2 inset). The Kd and Bmax for PACAP27 binding were 0.809±0.086 nM and 7.83±2.08 pmol/mg protein respectively. VIP, GHRH, glucagon and secretin did not displace $^{125}$I-PACAP27 binding. PACAP38 displaced $^{125}$I-PACAP27 binding more effectively than did PACAP27, but the displacement slope with unlabeled PACAP38 was parallel to that with unlabeled PACAP27. Scattered plot analysis of the displacement curve for PACAP 38 also indicated the existence of a single class of binding sites. Although PACAP38 had a significantly higher (about 10 fold) affinity for the receptor than PACAP27, there was no significant difference in Bmax between PACAP27 and PACAP38, suggesting that these peptides share the same binding site but with different affinities. Therefore, additional Scatchard plot analysis was performed analyzing both displacement curves for unlabeled PACAP27 and PACAP38 simultaneously assuming that PACAP27 and PACAP38 share the same binding site. There were no significant differences in Kd and Bmax estimated by these 3 analyses. The Kds for PACAP27 and PACAP38 in the E18 brain membrane preparations were comparable to those in membrane preparations from adult rat hypothalamus and pituitary. Gottschall, et al., Endocrinology 127: 272–277 (1990) and Gottschall, et al., *FASEB J* 5: 194–199. The Kds for either PACAP27 or PACAP38 remained unchanged throughout development. Binding sites for PACAP were detected in brain as early as on day E14, when Bmax was 1.96±0.33 pmol/mg protein which is approximately 1/14 of the Bmax in brain at 1 MO. It is noteworthy that the number of binding site at E14 is more than 100 times greater than that for VIP even in adult rat brain, and gradually increased throughout pre- and postnatal development from E14 to 1 MO (FIG. 3).

Figure 4:
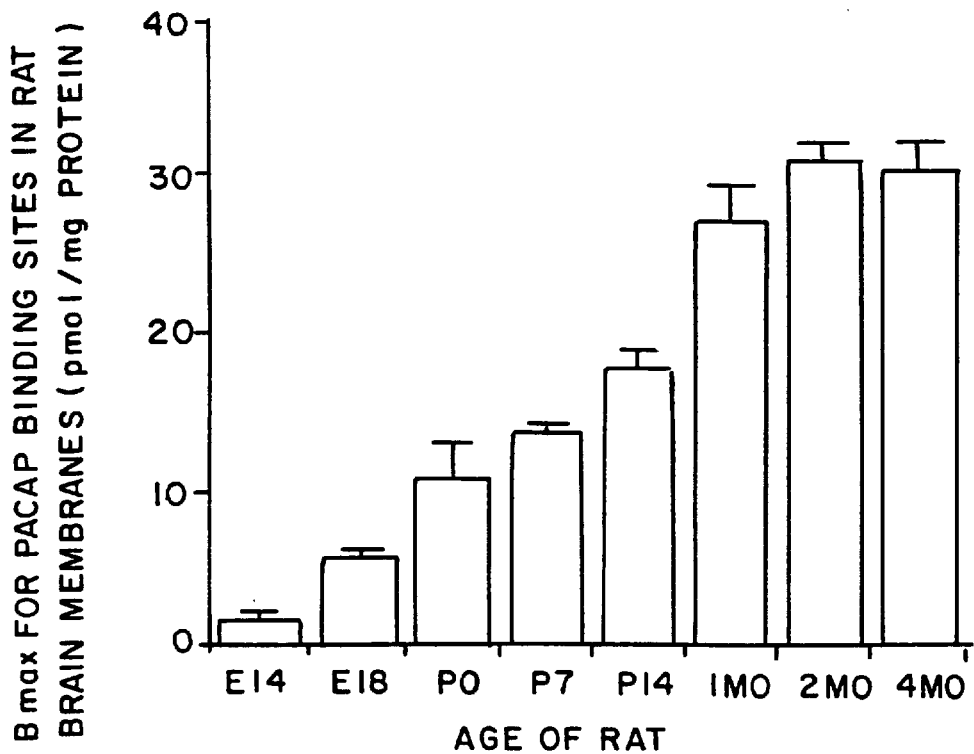
FIG. 4. shows concentrations of PACAP38 in rat brain during development. PACAP38 was determined by RIA. Arimura, et al., *Endocrinology* 129: 2787–2789 (1991). Each point represents mean±SEM (n=6). P indicates postmortal.

PACAP38 is immunoreactivity determined by RIA was detected (2.1±1.1 pg/mg wet tissue) in the whole brain extracts at E14. The concentration of PACAP38 in the whole brain, hippocampus, neocortex, and cerebellum gradually increased throughout the pre- and postanal period, reaching the highest levels between 1 and 4 MO, and then declining. It was noted that PACAP 38 immunoreactivity in the diencephalon rapidly increased between E18 and PO, and then increased more slowly throughout the postnatal period to reach a peak at 1 MO (FIG. 4).

EXAMPLE 2

Prevention of Natural Neuronal Cell Death in Chick Embryo

Effect of PACAP on natural neuronal cell death was also examined in chick embryos using similar experimental procedures described by Hamburger and Montalcini. Hamburger, et al., *J. Exp. Zool.* 11: 457–502. Fertilized White Leghorn eggs (Troslow Farms) were incubated at 39 C. at 99% humidity. A small hole was opened at the top of the egg on E3 ½ (Stage 23) by punching with microdissecting tweezers. One μl/g of egg weight of sterile Tyrode solution or solution containing 5 μM or 25 μM PACAP38 was administered daily through the hole onto the highly vascularized chorioallantoic membrane from day E3 ½ through E8 ½ in the experiment for dorsal root ganglion (DRG), and from E6 through E9 for lumbar motor column (LMC). This achieved a concentration of 5 nM or 25 nM PACAP throughout the egg, respectively, assuming free and uniform diffusion. Since massive degeneration of the dorsomedial (DM) population of DRG18 occurs between E7 ½ and E10, the embryos were sacrificed on E9 (Stage 35) in the experiment for DRG. The embryos were weighed and staged by measuring the toe length. Hamburger, et al., *Journal of Morphology* 88: 49–92. It should be noted that the experiment was designed so that the treatment began after the period of extensive neural proliferation in the embryo. This ensured that any increase in cell number was due to a prevention of natural cell death, not a stimulation of mitoses.

In each embryo, a large portion of tissue between the cervical and lumbar regions of the spinal cord was removed and placed in Carnoy's fixative for two hours. Once fixed, the tissues were transferred directly to a thionine solution and stained en bloc for 15 hrs. The blocks were subjected to serial dehydration in graded alcohol and embedded in paraffin. Tissues were sectioned el at 10 μm, mounted on gelatin coated slides, deparaffinized, and cover slipped with Cytoseal.

The preparation of the lumbar column of the spinal cord was identical to that for the DRG18 study, with the following exceptions; The entire lumbar spinal column (segments 21–32) was removed, dissected free of skin, fixed in Carnoy's solution, stained, embedded in paraffin, serial sectioned, and mounted as before. Both the control and experimental groups were administered vehicle or PACAP38 respectively, daily from E6 through E9 using the same technique described above, and sacrificed on E10 (Stage 36).

To identify the individual RG18, the lower brachial and upper thoracic ganglia were reconstructed for each embryo. Reconstruction was achieved by marking the block, slide, row, and section numbers which corresponded to the first and last sections of the ganglia in each bloc. The brachial plexus was used as the primary landmark for DRG16 and the third ganglia from DRG 16 was identified as DRG18.

The LMC was reconstructed in a similar manner, by citing the bloc, slide, row and section numbers. The motor column stained very heavily compared to the rest of the spinal cord.

The magnification used (×400), one can observe DRG18 divided into two populations of cells: large differentiating ventrolateral (VL) and small, late differentiating dorsomedial (DM) cells. Although the boundary between the two populations of neurons was sometimes indistinct, it was possible to identify individual cells based upon their morphologies. In the VL population, the number of degenerating cells increased sharply beginning at E4 ½ (Stage 25) peaked at Stage 27 and then declined immediately. Hamburger, et al., Journal of Neuroendocrinology 1:60–71 (1981). In the DM population, a rapid increase in the number of degenerating cells began at stage 33; thus the degeneration periods for the VL and DM cells barely overlap. The peak of DM degeneration was reached within half a day, at stage 34, and a sharp decline began at stage 35. In the present example, only DM population of neurons was studied. Degenerating cells displayed varying morphologies from large vacuolated cells to mere fragments. However, most degenerating neurons appeared as deeply stained, homogenous spheres. Macrophages containing debris of several cells were encountered rarely and counted as two degenerating cells. Every second section of the ganglia was counted, and the sum multiplied by two to obtain a data point. A total of 6 ganglia were counted in each of the control and experimental groups, respectively.

In the lumbar motor column (LMC), intact motoneurons were easily distinguishable from surrounding cells due to their large size and deeply stained perikaryon. Only those neurons with an intact nuclear membrane and at least one visible nucleolus were counted as live cells. Every tenth section of the LMC was counted, and the sum of the sections multiplied by ten to obtain a data point. A total of 6 motor columns was counted in each of the control and experimental groups.

Figure 5:
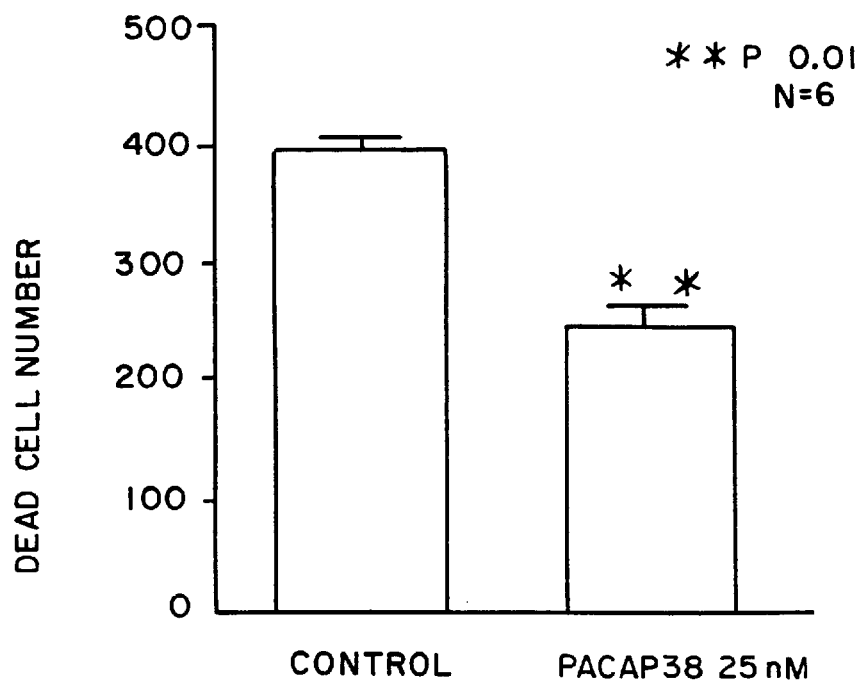
FIG. 5. shows the number of dead cells in the dorsomedial population of dorsal root ganglia (DRG18) in the chick embryo on day E9. The control group received vehicle and the experimental group received PACAP38 (25 nM in the egg) daily from E3 ½ to E8 ½. Number is the mean of the numbers of degenerating cells in 6 ganglia in each group. Bar indicates SEM.

Administration of PACAP38 (25 nM in the egg) to the chick embryo resulted in a pronounced reduction of the number of degenerating cells in the DM population of neurons in DRG18 on E9, as compared with the untreated control group (FIG. 5). The number of the degenerating cells in the PACAP38-treated embryos was 37.2% less than that in the untreated embryos. The difference was highly significant ($p<0.01$).

Figure 6:
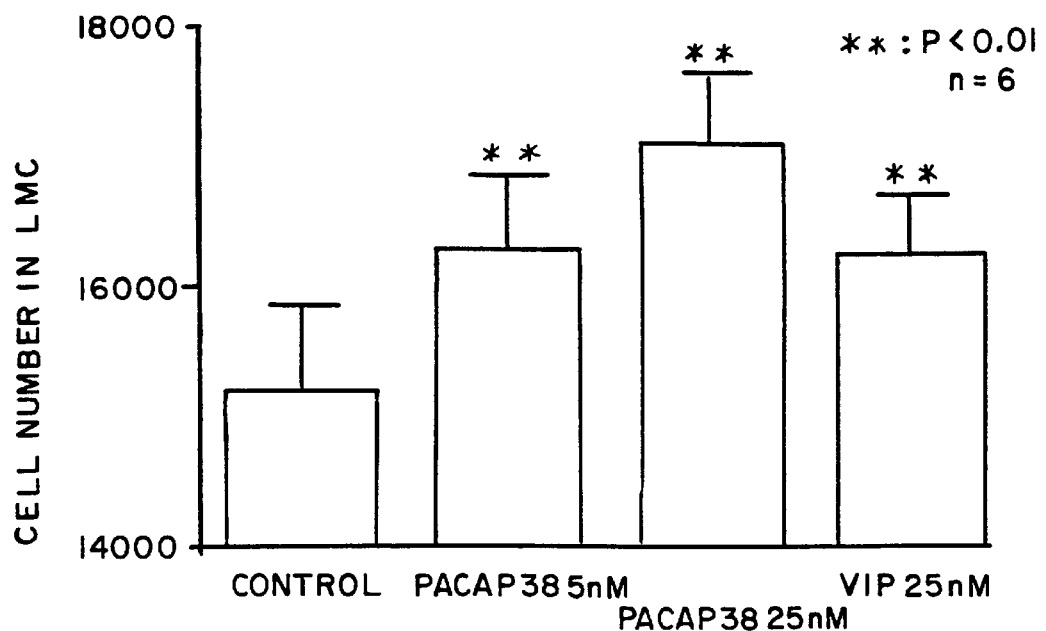
FIG. 6. shows the number of viable motoneurons in the lateral motor column (LMC) of chick embryos on E10. Embryos received vehicle, or 5 nM or 25 nM PACAP (concentrations in the egg after injection) daily from E6 to E9. Average LMC is represented by 320–340 sections and cell counts were made on every tenth section. Sum of live cells in all counted sections multiplied by 10 is shown in this figure. Numbers indicate mean numbers of live cells in 6 LMC in each group. Bars indicate SME.
Figure 7:
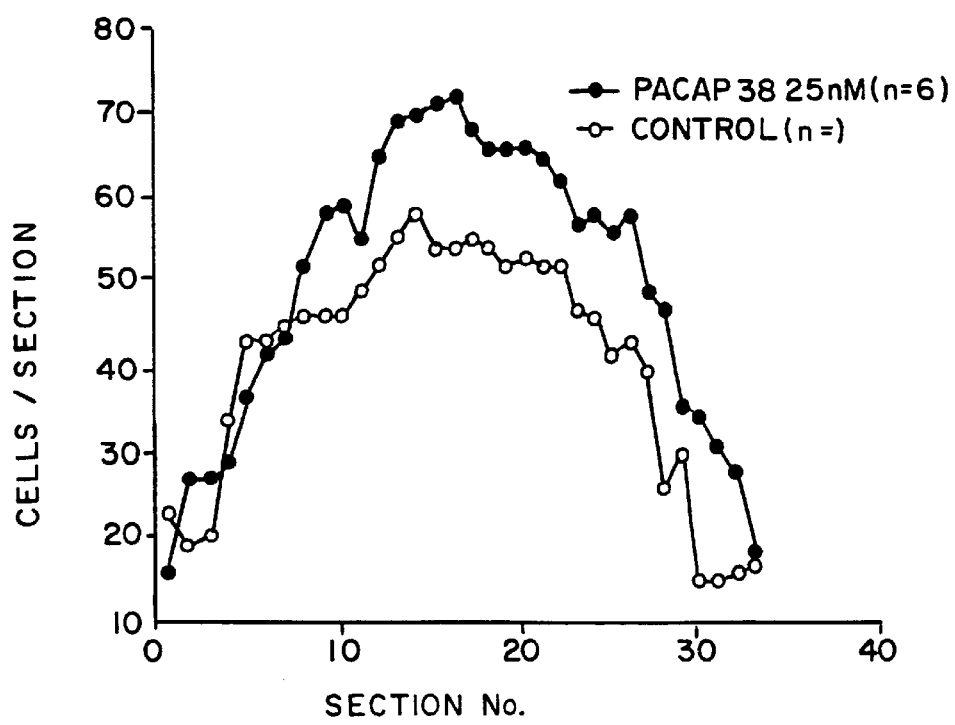
FIG. 7. shows distribution of motoneurons across LMC in chick embryos at E10. Mean of motoneuron numbers per section of 1–9 segments of lumbar column of vehicle (open circle) and 25 nM PACAP treated (close circle) embryos. Note the difference is obvious only in the middle and mid-caudal segments.

Administration of PACAP38 at 5 nM and 25 nM also resulted in a significant increase in the number of motoneurons per motor column by 7.2% and 12.5% respectively on E10 (FIG. 6). Therefore, the response appeared to be dose-dependent, and selective motoneurons within the central portion of the lumbar LMC (FIG. 7).

These findings resemble the effect of NGF on the survival of otherwise naturally degenerating sensory neurons. PACAP38 increased the survival of both sensory and motoneurons during the embryonic development of chick embryo.

Since the biological effect of a peptide is mediated by the initial interaction between the peptide and its receptor, it is possible that the chick embryos at stage 23–34 express the receptors for PACAP38. As demonstrated in rat embryos, Tatsuno, et al., *Peptides* 15: 55–60, PACAP and its receptors appear to be expressed in chick embryos. The primary structure of chick PACAP is different from PACAP of mammals including rat, sheep and humans by only one amino acid (Yasuhara, et al., *Reg. Peptides* 37: 326 (1992), suggesting that the structure of PACAP is well conserved throughout phylogeny, and thus may play an important role for survival of neurons of animals and humans.

Presence of PACAP containing cells in DRG, and a dense network of PACAP containing nerve fibers in the dorsal horn of the spinal cord were demonstrated in adult rats by immunohistochemistry. Legradi, et al., *22nd Ann. Mtng. Soc. for Neurosci* 18, part 1: abstr 48.5 (1992). In the lumbar spinal cord, PACAP fibers were also observed in the ventral horn. Immunohistochemistry at the electronmicroscopic level revealed the presence of synapses between PACAP-positive axon and PACAP-negative dendrites in the dorsal horn of the rat spinal cord. Legradi, et al., *22nd Ann. Mtng. Soc. for Neurosci* 18, part 1: abstr 48.5 (1992). Electrophysiological studies using an organ culture of rat DRG showed that neurons in the DRG are depolarized by PACAP due to increased permeability to Cl and that the same neurons are also depolarized by GABA, an inhibitory neurotransmitter, suggesting that PACAP is an inhibitory synaptic transmitter. Curte, D., and E. Perl, *Soc for Neuroscience abstr.:* 636.11 (1993). Therefore, PACAP may play a physiological role as a neurotransmitter in the spinal cord and possibly in the brain, but in addition the peptide appears to play a role as a neurotrophic survival factor for the spinal cord neurons even in adult animals. Structurally homologous VIP increases survival of cultured spinal neurons. Brenneman, et al., *Peptides* 6: 35–39.

EXAMPLE 3

Prevention of Neuronal Cell Death Induced by gp120

Psychoneurological symptoms are commonly observed in patients with acquired immunodeficiency syndrome (AIDS). Snider, et al., *Ann. Neurol.* 14: 403–418 (1983) and Brenneman, et al., *Internatl. Review of Neurobiol.* 32: 305–353 (1990). A basic characteristic of AIDS is the presence of relatively few human immunodeficiency virus (HIV)-infected cells, yet both the immune and nervous system can develop catastrophic functional impairment. This observation has led to the search for indirect mechanisms of HIV-related toxicity rather than direct damage due to viral infection of individual cells. A leading candidate for a cytotoxic product of HIV is the major external envelop protein, gp120. In 1988, purified gp120 from various HIV isolated was shown to produce neuronal toxicity in dissociated hippocampal cultures derived from fetal mice. Brenneman, et al., *Nature* 335: 639–642 (1988). The neuronal cell killing action was observed at extraordinarily low concentrations (0.01–1 pM). Neurotoxicity has also been observed after treatment with gp120 in other CNS preparations from rodents. Dreyer, et al., *Science* 248: 364–367 (1990). Previous studies reported that HIV-infected cells secrete gp120 (Schneider, et al., *J. Gen. Virol.* 67: 2533–2538 (1986)), and gp120-like biological activity has been reported in the CSF of AIDS patients. Buzy, et al. *Brain Res.* 598: 10–18 (1992).

Neuronal cell death associated with gp120 treatment of murine hippocampal cultures has been shown to be potently and completely prevented by VIP (Brenneman, et al., *Nature* 335: 639–642 (1988)) and by peptide T. Brenneman, et al., *Drug Develop. Res.* 15: 361–369 (1988).

Figure 8:
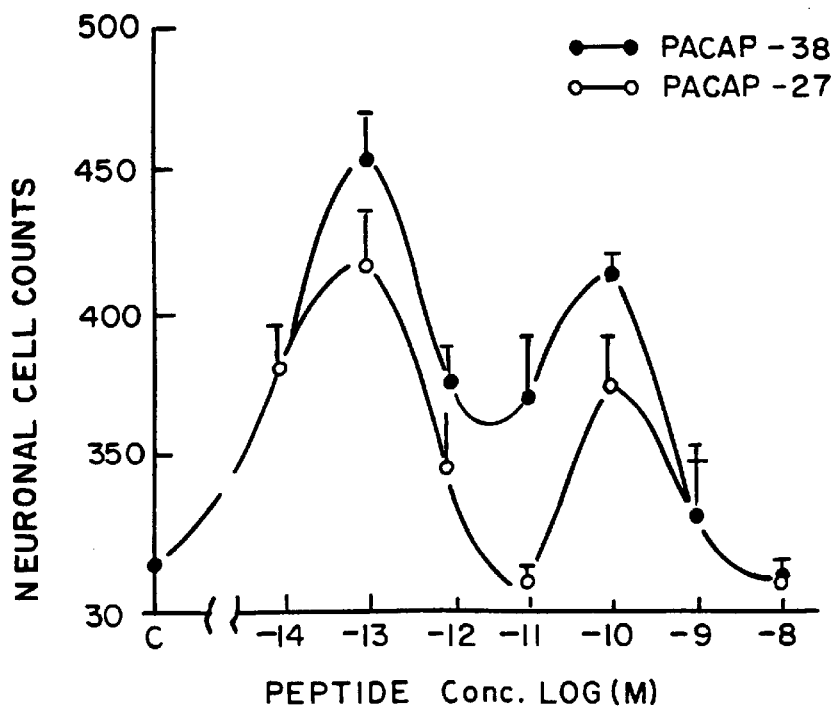
FIG. 8. shows the comparison of PACAP38 and PACAP27: prevention of gp120-induced neuronal cell death in dissociated hippocampal cultures. The cultures were prepared from 16–17 day-old mice embryos (C57B1/6) as previously described. Brenneman, et al., *Nature* 335: 639–642 (1988). Before treatment, the cultures were given a complete change of medium. One week old cultures were treated for five days with 1 pM gp120 (RFII isolate) and either PACAP38 (closed circles) or PACAP27 (open circles). Cell counts were conducted on 60 fields, 0.12 mm$^2$ each. Neurons were identified immunocytochemically using antiserum against neuron specific enolase. Schmechel, et al., *Nature* 276: 834–836 (1978). Each value is the mean of 3–5 dishes. Error bar represents the standard error. Control cultures had 404±5 cells. In comparison to cultures treated with pg120 alone, significant increases in cell counts were observed at 0.01 to 100 pM PACAP38 and at 0.01, 0.1 and 100 pM PACAP27 (P<0.01). Treatment with gp120 alone produced at 21% decrease in cell counts in comparison to controls (P<0.001).

In view of the substantial sequence homology between VIP and PACAP (Miyata, et al., *Biochem. Biophys, Res. Commun.* 164: 567–574 (1989)), and the greater potency of PACAP than VIP in adenylate cyclase activation in various cell types (Miyata et al., *Biochem Biophys. Res. Commun.* 164: 567–574 (1989); Miyata, et al., *Biochem Biophys. Res. Commun.* 170: 643–648 (1990); and Deutsch, et al., *J. Biol. Chem.* 267: 5108–5113 (1992)), the possible effect of PACAP on gp120-induced death in hippocampal neurons was examined under similar experimental conditions as described for the VIP studies. Brenneman, et al. *Nature* 335: 639–642 (1988). One-week old cultures were treated for five days with 1 pM of gp120 or gp120 plus various concentrations of PACAP38 or PACAP27 (FIG. 8). Both peptides attenuated the neuronal cell death associated with gp120 treatment and both peptides exhibited bimodal dose-response curves with peaks at 0.1 pM and 0.1 nM. Previous results showed that 0.1 nM VIP prevented neuronal death in gp 120-treated cultures. Brenneman, et al. *Nature* 335: 639–642 (1988). Thus, both PACAP forms can elicit a cytoprotective action similar to that of VIP, although the bimodal response suggests a more complicated mechanism, probably involving more than one type of receptor. In this regard, VIP will bind to a Type I PACAP receptor at an affinity that is 1000 times less than that of PACAP; in contrast, PACAP binds to Type II PACAP receptors with similar affinity as VIP. Arimura, et al., *Trends Endocr. Metab.* 3: 288–294 (1993). Arimura et al., *Ann NY Acad. Sci.* 739:228–243 (1994). It is possible that the PACAP-induced cytoprotective action observed at 0.1 nM may occur through Type II PACAP or VIP receptors and the activity seen at 0.1 pM may result from an interaction through Type I PACAP receptor. Regardless of the phenotype of the receptors, PACAP like VIP increases the survival of developing hippocampal neurons exposed to lethal concentrations of the HIV envelope protein.

EXAMPLE 4

Figure 9:
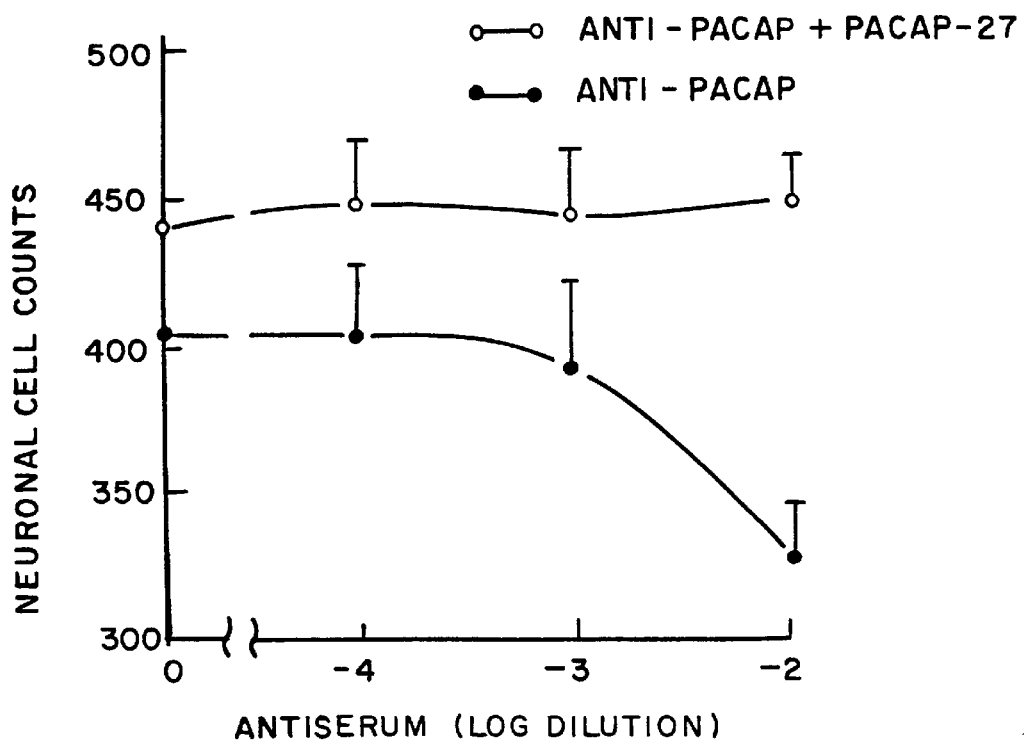
FIG. 9. shows antiserum to PACAP27 produced neuronal cell death in dissociated hippocampal cultures: prevention by PACAP27. Antiserum was obtained from rabbits as described previously. Arimura, et al., *Endocrinology* 129: 2787–2789 (1991). A comparison was made between cultures treated with antiserum alone (closed circles) and dishes given antiserum plus 0.1 nM PACAP27 (open circles). The experimental conditions were the same as that described in FIG. 7. Each value is the mean of 3–5 dishes. The error bar is the standard error. A significant decrease from control was observed at 1:100 antiserum dilution (P<0.001). Co-treatment with 0.1 nM PACAP27 prevented the cell loss associated with 1:100 anti-PACAP27. Treatment with PACAP27 alone produced a significant increase from control (P<0.05). Cell counts for control cultures was 400±5 in 60 fields.

Having shown that PACAP peptides have a cytoprotective effect from gp120, we next examined the potential role of endogenous PACAP as a survival-promoting factor in the hippocampal cultures. To test this possibility, neutralizing antiserum against PACAP27 (Koves, et al., *Neuroendocrinology* 54: 159–169 (1991) and Arimura, et al., *Endocrinology* 129: 2787–2789 (1991)) was incubated with the cultures for five days to block the activity of endogenous peptide. Antiserum at various dilutions was added to the cultures with or without the presence of 0.1 nM PACAP27. Addition of the antiserum alone reduced the number of neurons at 1:100 dilution (FIG. 9). The cell loss associated with the antiserum was prevented by co-treatment with PACAP27. Treatment with PACAP27 alone produced a small increase in cell counts in comparison to control cultures (FIG. 9). These findings suggest that endogenous PACAP plays a role in the survival of hippocampal neurons in vitro.

Figure 10A:
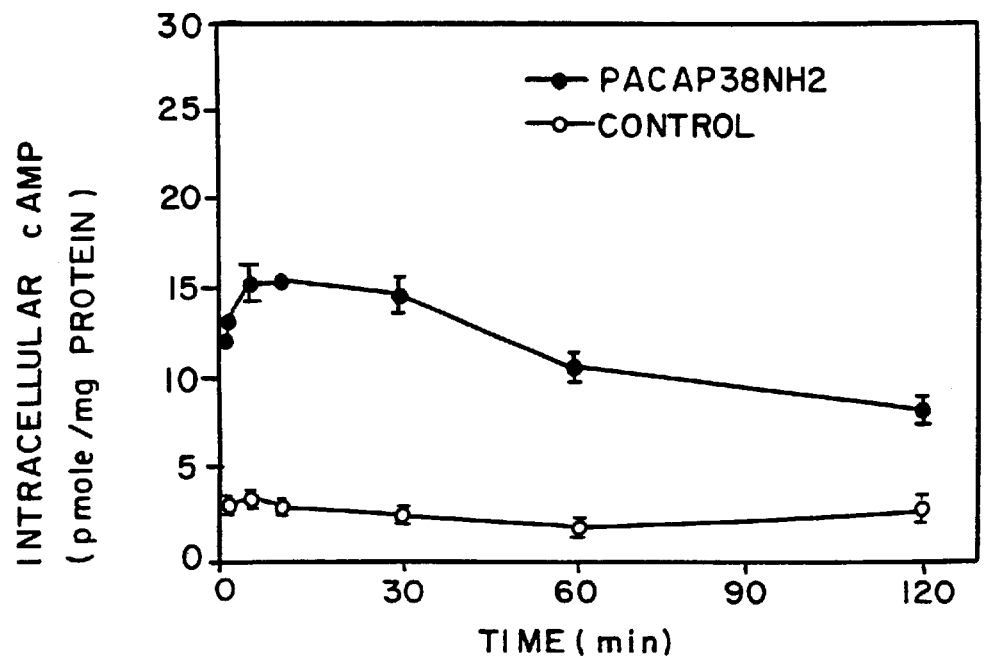
FIGS. 10A and 10B are graphs showing cAMP response to PACAP in cultured rat neurons. Neuron cultures were prepared from brains of 1 day-old rats. 1×10$^7$ cells were plated in each dish (35 mm diameter). Neurons were cultured for two weeks before experiment. cAMP in cells were determined by RIA various time intervals after addition of PACAP.
Figure 10B:
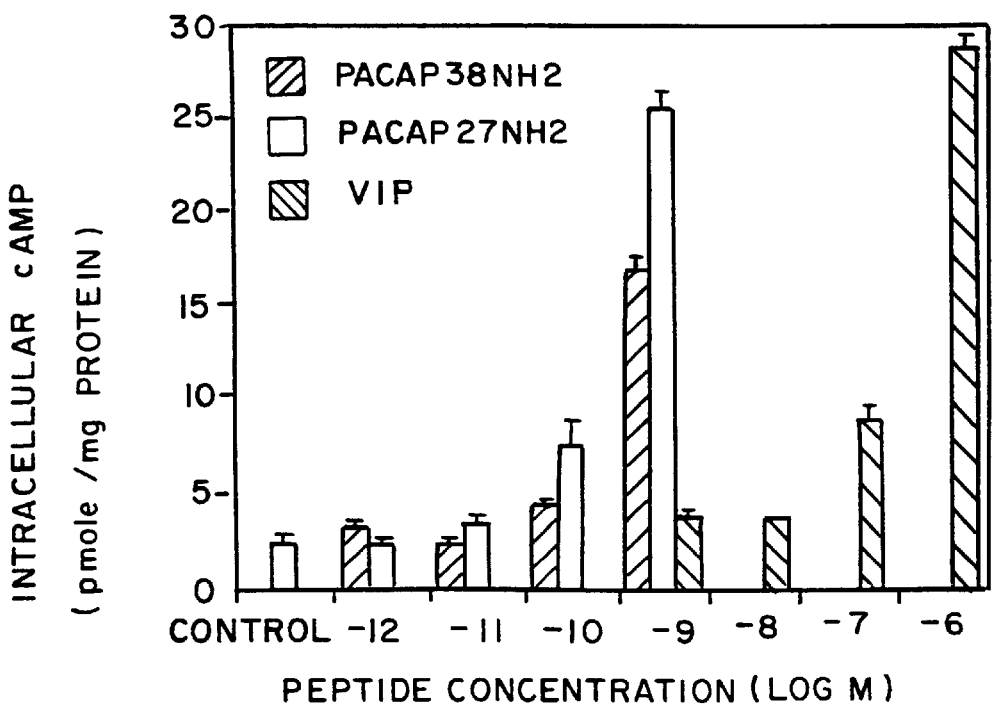
Figure 12:
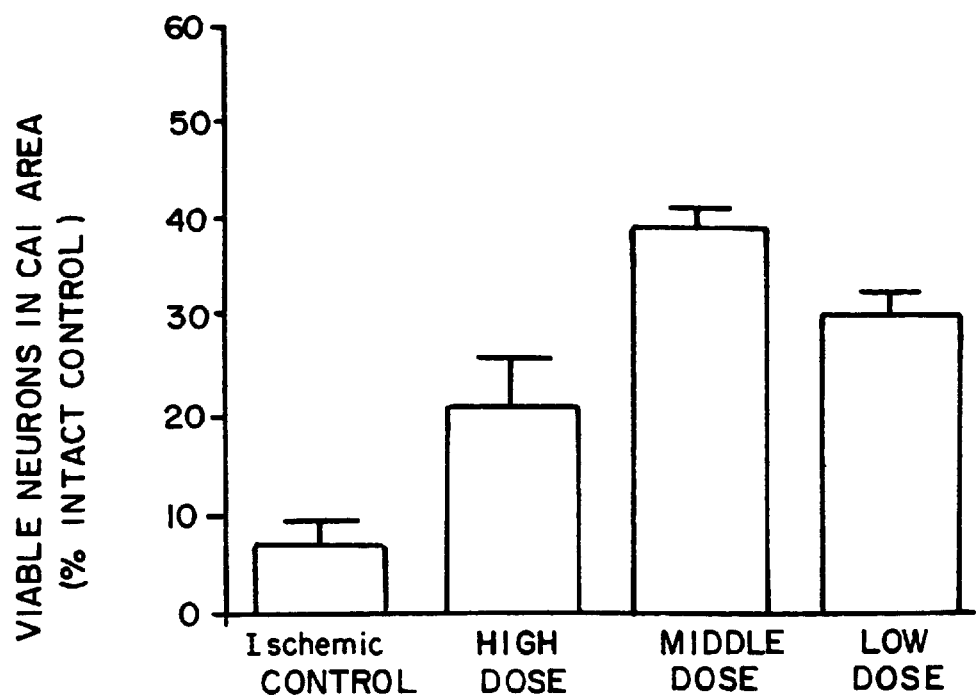
FIG. 12 is a graph showing the prevention of ischemia induced neuronal cell death in rat hippocampus using PACAP38. Each column indicates viable cell number 7 days after 15 min ischemia of the forebrain of rats which were intracerebroventricularly administered the vehicle alone or the vehicle containing varying amounts of PACAP38. The numbers of cells are expressed by percentages of live cells as compared with the cells in the same area of the intact rat hippocampus. In this experiment, a bolus administration of 450 ng PACAP 38/10 µl H$_2$O over 10 min followed by continuous infusion of the peptide at 45 ng/µl/hr over seven days was the most effective in cytoprotection. The higher dose was less effective.

Although both VIP and PACAP are recognized to stimulate the formation of cAMP (Arimura, et al., Regul. Peptides 37: 287–303 (1992) and Gozes, et al., *Mol. Neurobiol* 3:21 (1989)), the second messenger mediating the cytoprotective and survival-promoting actions of VIP and PACAP does not necessarily utilize this signal transduction pathway. Both PACAP38 and PACAP27 elevate intra- and extracellular cAMP in a dose-related manner in a range of 10 pM to 10 nM in rat neurons and astrocyte cultures (FIGS. 10 and 11). The neuronal cultures showed a more rapid cAMP response to PACAP than the astrocyte cultures, but the magnitude of the intracellular accumulation of cAMP in astrocyte cultures (expressed in pmol/mg cellular protein) was about 14 times greater than the response in neurons. VIP also increased cellular cAMP in both neuron and astrocyte cultures, but the activity was approximately 1000 times less potent than PACAP. Importantly, no increases in cAMP for any CNS culture system has been observed at the concentrations of peptide that increase neuronal survival: 0.1 pM PACAP and 0.1 nM VIP. In fact, these concentrations of peptide are 100–1000 times smaller than that required to produce measurable increases in cAMP for CNS cultures. These data strongly suggest that the cytoprotective action of PACAP and VIP are mediated by a second messenger other than cAMP. In this regard, both PACAP and VIP have been shown to produce increase in intracellular calcium at 1–100 pM in neurons (Tatsuno, et al., *Endocrinology* 131: 73–81 (1992)) and astrocytes (Fatatis, et al., *Proc natl. Acad. Sci. USA,* 91: 2036–2040 (1994)). PACAP has also been shown to increase intracellular calcium in pancreatic β-cells at 0.01–0.1 pM. Yada, et al., *J. Biol. Chem.* 269: 1290–1293 (1994). We would speculate that the increase in intracellular calcium produced by these peptides plays a primary role in the cytoprotective and survival-promoting action of both PACAP and VIP.

EXAMPLE 5

Animal Model for Ischemia-Reperfusion-Induced Neuronal Cell Death in the Brain In order to evaluate the cytoprotective action of a substance in vivo, an animal model has been used which produces an extent of neuronal cell damage similar to that produced in all experimental animals. The method used herein to produce consistent neuronal cell damage in the CA1 of the hippocampus by occlusion of the four brain vessels was originally described by Pulsinelli et al. *Stroke*, 10:267–272 (1979).

Adult male rats of CD strain weighing 270–300 g body weight (Charles River Breeding labs, Wilmington, Miss.) were used. Under Ketamine anesthesia, the bilateral vertebrate arteries were permanently occluded at the first cervical vertebra by electrocoagulation. Bilateral carotid arteries were exposed and a loop of silicon rubber tubing was placed around each carotid artery, leaving the end of the tubing outside the suture. The animal was left in the laboratory with water, but without food. The following morning, both loops around the carotid arteries were pulled and artery clips were applied on the loops at the portion close to the skin so that both carotid arteries were occluded and ischemia of the brain occurred as long as the clips remained. The clips were removed 15 minutes later. During ischemia, body temperature was monitored by thermometer placed in the rectum and the body temperature was maintained at 37° C. by radiation heat from light bulb. Only in the animals which became unconscious was effective ischemia considered to have occurred. Reperfusion of bilateral carotid arteries was assured by direct visual examination. The incision wound was closed.

Method of Administration of Peptide

Soon after the reperfusion of the carotid arteries began, the animal was placed on a stereotaxic instrument, the skull was exposed, and a small hole was made by a dental drill at anterior 0.6 lateral 1.5, vertical 5.0 mm from the bregma and skull surface, and guided cannula (Alza Corp., Palo Alto, Calif.) was inserted into the hole so that the tip of the cannula is in the lateral cerebroventricle and fixed on the skull by dental cement. The incised skin was then closed by suture. Then 10 $\mu$l of artificial cerebrospinal fluid (CSF) containing 0.1% bovine serum albumin (ESA) or the vehicle containing varying amounts of PACAP38 was introduced.

EXAMPLE 6

Figure 14:
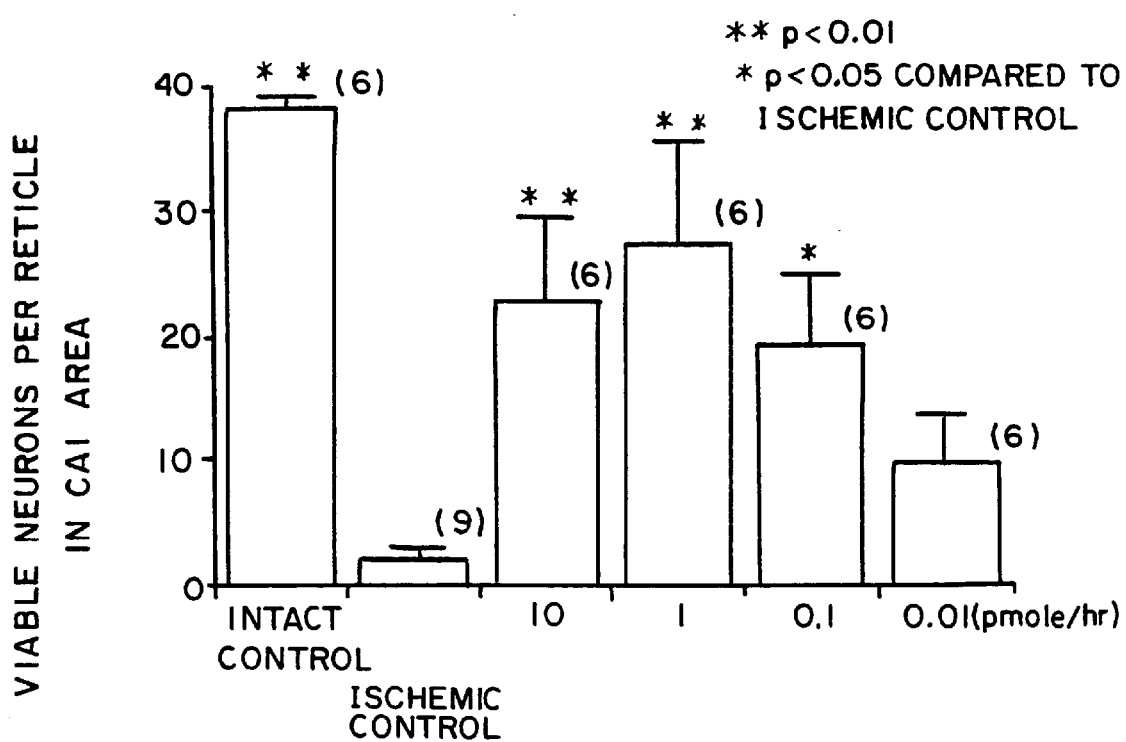
FIG. 14. is a graph similar to FIG. 12, showing the prevention of ischemia-induced neuronal cell death in rat hippocampus using PACAP38 as described in Example 6.
Figure 13A:
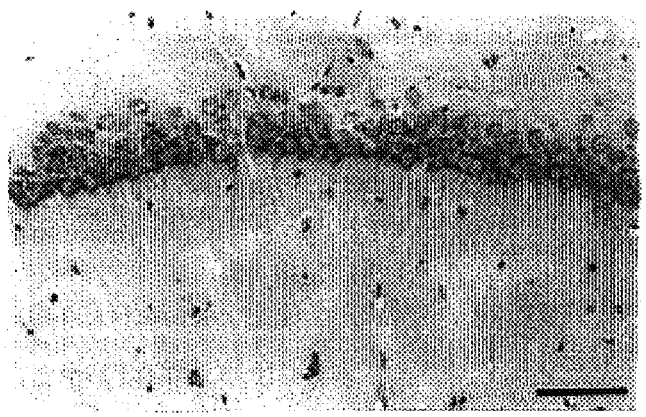
FIGS. 13A–F are microphotographs of coronal sections of the right hippocampal CA1 from intact rats and rats subjected to forebrain ischemia for 15 min. The sections were stained with cresyl violet (A, B, C) and immunostained for MAPII (D, E, F). A, D: Intact rats. B, E: 7 days after ischemia in vehicle-infused (icv) rats. Note severe damage to pyramidal cells in CA1 (B), and marked decrease in MAPII immunoreactivity in the denditric fields of the CA1 area (E). C, F: 7 days after ischemia in rats infused with PACAP38 icv by an implanted osmotic pump over one week at 1 pmol/h. PACAP38 administration started immediately after ischemia. Treatment with PACAP38 prevented ischemia-induced cell death in CA1 (C) and preserved MAPII immunoreactivity (dendritic processes) in CA1 area (F). Bar=100 µm in A, B, and C, and 200 µm in D, E, and F.
Figure 13B:
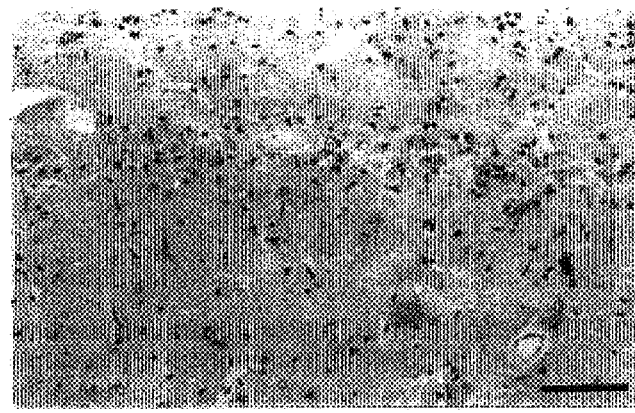
Figure 13C:
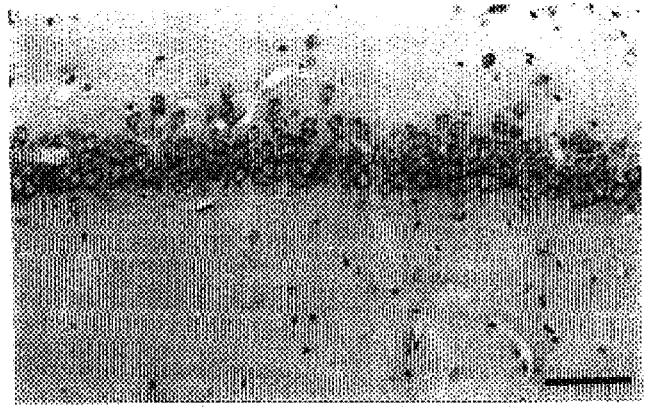
Figure 13D:
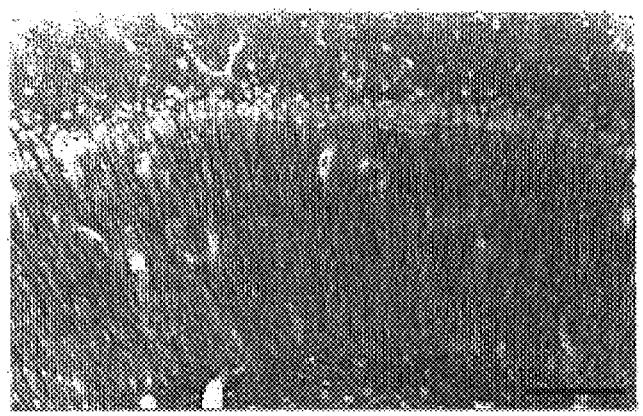
Figure 13E:
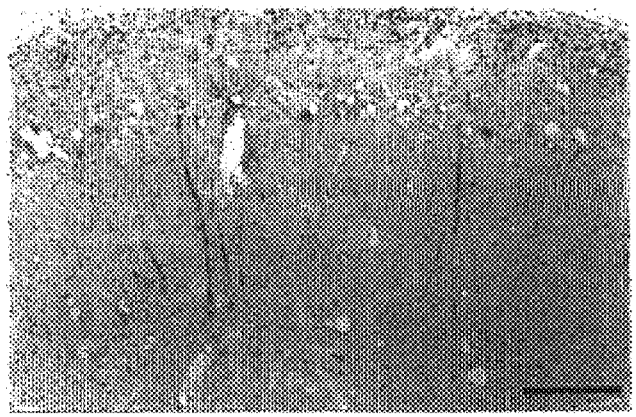
Figure 13F:
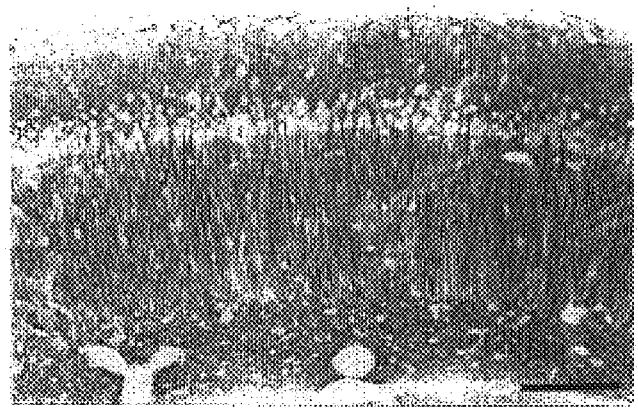

This example includes data of the effect of intracerebroventricular (icv) administration of PACAP38 on the neuronal cell death in the hippocampus induced by ischemia-reperfusion in rats. In this study lower doses than 10 pmol/h (the most effective dose in the last study), e.g. 1, 0.1 and 0.01 pmol/h over 7 days were tested. As shown in the FIG. 14, 1 pmol/h was the most effective, though the difference from 10 pmol/h is statistically insignificant.

EXAMPLE 7

PACAP Concentrations in Brain Tissues

Figure 15:
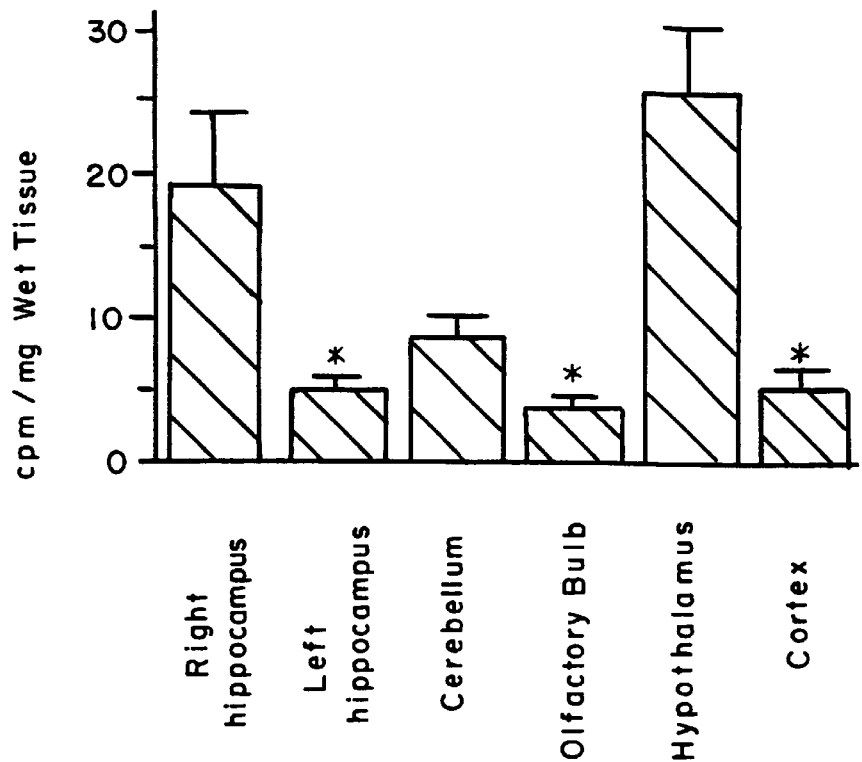
FIG. 15 is a graph showing $^{125}$I-PACAP 38 levels in brain tissue 10 minutes after icv injection, at 1×10$^6$ cpm $^{125}$I-PACAP38.

The range of concentrations of PACAP in the brain tissue after Intracerbroventricular (icv) infusion of the peptide was calculated. This calculation was based on the transport of $^{125}$I-labelled peptide given icv as a bolus but slow injection over 5 min. $1 \times 10^6$ cpm $^{125}$I-PACAP38 was injected icv in anesthetized rats, the cpm in the brain tissues 10 min after the injection is shown in FIG. 15.

The labelled peptide was injected into the right lateral ventricle. As shown in FIG. 15, the right hippocampus contained 20 cpm per mg tissue, while only 5 cpm per mg tissue in the left, indicating that PACAP injected icv was not evenly distributed throughout the brain tissues. These results indicate that 1/200–1/50 of the amount of PACAP injected icv was transported into 1 g (ml) of hippocampal tissue.

EXAMPLE 8

Figure 16:
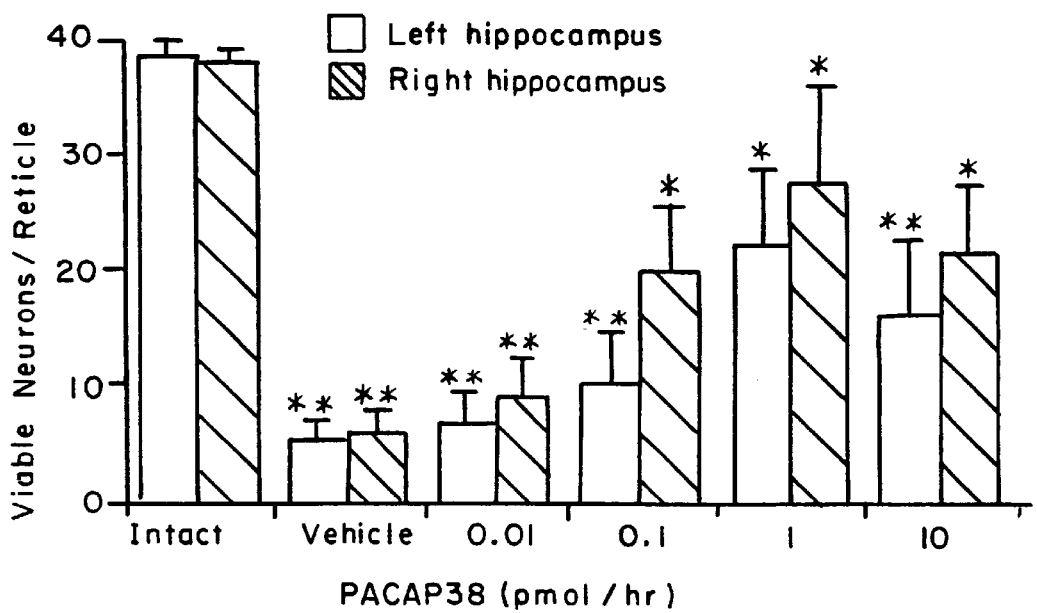
FIG. 16 is a graph showing the effects of icv infusion of PACAP38 into the right lateral cerebroventricle on ischemia-induced neuronal cell death in the hippocampal CA1 in rats. The ordinate shows the mean number±SE of viable neurons per reticle (220 µm) 7 days after ischemia.

Effects of ICV Infusion of PACAP38 on Ischemia-Induced Neuronal Cell Death in the Hippocampal CA1 in Rats PACAP38 was icv infused into the right lateral cerebroventricle of rats having neuronal cell damage in the CA1 of the hippocampus as discussed in example 5. The effect of the icv infusion of PACAP38 on ischemia-induced neuronal cell death in the hippocampal CA1 in rats was measured. The results are shown in FIG. 16. The ordinate shows the mean number±SE of viable neurons per reticle (220 $\mu$m) 7 days after ischemia. Vehicle-treated rats showed marked neuronal cell death in both right and left hippocampus. ICV infusion of PACAP38 over one week significantly prevented the neuronal cell death. The dose-response curve of the cytoprotective effect was bell-shaped with the maximum effect at 1 pmol/hr. Although there was no significant difference, the cytoprotective effect in the right side appeared to be greater than in the left side, n=6–7.+: $p<0.05$ vs vehicle; *:$p<0.05$ vs intact; **: $p<0.01$ vs intact. Student-Newman-Keuls test was used for all analyses.

EXAMPLE 8

Figure 17:
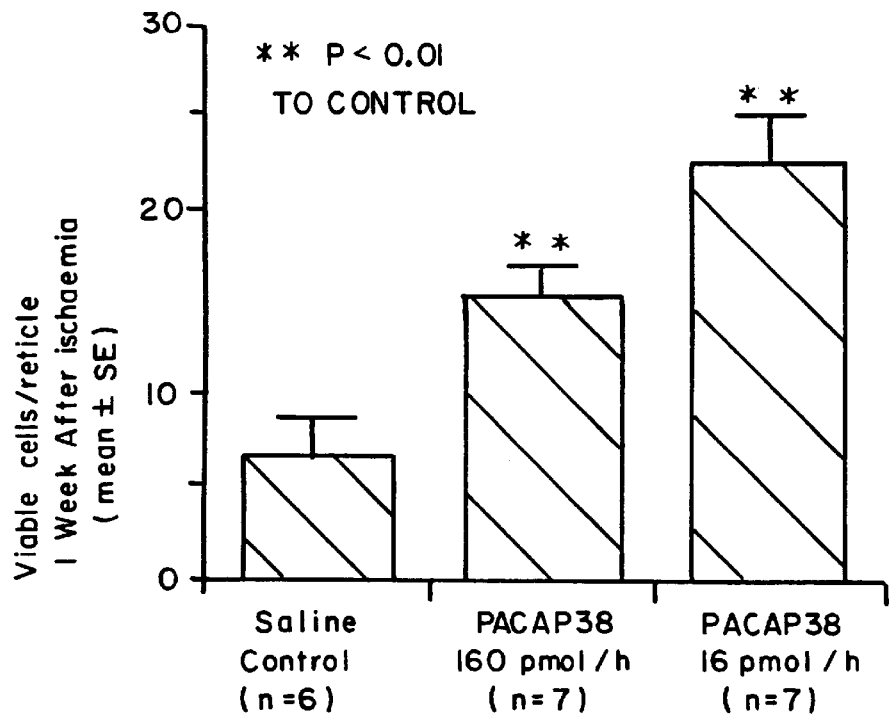
FIG. 17 is a graph showing the cytoprotective effect of iv infusion of PACAP38 which started immediately after ischemia in rats. Both 160 pmol/hr and 16 pmol/hr PACAP38 significantly attenuated ischemia-induced neuronal cell death in CA1 7 days after ischemia. The small dose of PACAP38 appeared to exhibit greater effect.

Effects of IV Administration of PACAP38 on Ischemia-Induced Neuronal Cell Death in the Hippocampal CA1 in Rats PACAP38 was administered i.v. to rats (see example 5) over one week, starting immediately after ischemia/reperfusion. As shown in FIG. 17, i.v. administration of the peptide significantly attenuated neuronal cell death induced by forebrain ischemia. The magnitude of the cytoprotective effect following iv administration of PACAP38 was very similar to that for icv administration (compare FIG. 16 and FIG. 17). Two i.v. does of 16 to 160 pmol/hr (16 and 160 times greater than the icv dose) were tested and both attenuated neuronal cell death significantly (<0.01). In this experiment, 20 $\mu$g/kg (approximately 4 nmol/kg) was given as a bolus iv injection before the infusion began. The initial bolus injection was given in an attempt to saturate possible binding sites of a presumed binding protein in the blood (preliminary study suggested its presence).

EXAMPLE 9

Figure 18:
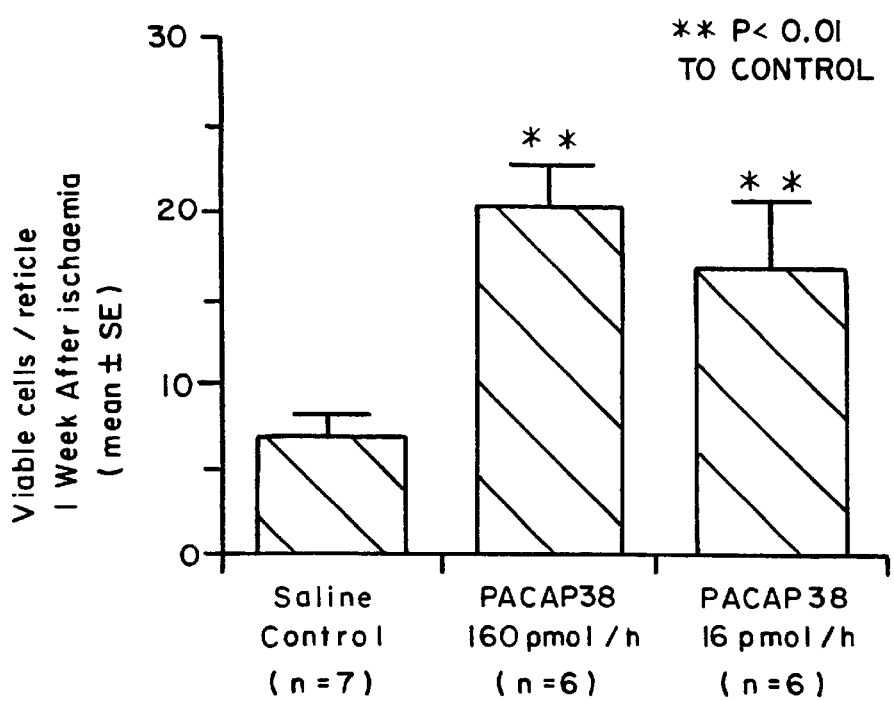
FIG. 18 is a graph showing the cytoprotective effect of iv infusion of PACAP38 which started 24 hrs. after ischemia in rats. Both 16 pmol/hr and 160 pmol/hr PACAP38 significantly attenuated ischemia-induced neuronal cell death in CA1 7 days after ischemia.

Effects of IV Administration of PACAP38 on Ischemia-Induced Neuronal Cell Death 24 Hours After Ishemia Neuronal cell death in CA1 induced by forebrain ischemia progresses slowly. One day after ischemia/reperfusion many viable neurons were still seen in CA1. However, nearly all neurons died one week after ischemia. Therefore, if the administration of PACAP38 is started 24 hrs after ischemia, the treatment could possibly still prevent the slow death of the neurons. To test this hypothesis, a bolus iv injection and subsequent iv infusion of PACAP38 was started 24 hrs after ischemia. As shown in FIG. 18, the treatment significantly (<0.01) attenuated brain cell death. Both 16 pmol/hr and 160 pmol/hr were equally effective.

In summary, neuronal cell death in the hippocampus resulting from forebrain ischemia/reperfusion in rats was significantly attenuated by iv infusion of PACAP38. Administration beginning 24 hrs after the ischemia/reperfusion was as effective as infusion starting immediately after the ischemia/reperfusion.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A method of preventing or attenuating neuronal cell death comprising continuously administering to a subject in need thereof a compound selected from the group consisting of:

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-NH$_2$ (SEQ ID NO:3),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-OH (SEQ ID NO:4),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-NH$_2$ (SEQ ID NO:5),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-OH (SEQ ID NO:6),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-NH$_2$ (SEQ ID NO:7),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-OH (SEQ ID NO:8),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-NH$_2$ (SEQ ID NO:9),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-OH (SEQ ID NO:10),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-NH$_2$ (SEQ ID NO:11),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-OH (SEQ ID NO:12),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-NH$_2$ (SEQ ID NO:13),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-OH (SEQ ID NO:14),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-NH$_2$ (SEQ ID NO:15),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-OH (SEQ ID NO:16),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -NH$_2$ (SEQ ID NO:17),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -OH (SEQ ID NO:18),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-NH$_2$ (SEQ ID NO:19),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-OH (SEQ ID NO:20),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-Lys-NH$_2$ (SEQ ID NO:21),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-Lys-OH (SEQ ID NO:22),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-Lys-Asn-NH$_2$ (SEQ ID NO:23),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-Lys-Asn-OH (SEQ ID NO:24),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-Lys-Asn-Lys-NH$_2$ (SEQ ID NO:25), and X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg -Val-Lys-Asn-Lys-OH (SEQ ID NO:26), wherein:

X is NHR, where R is H or a solubility effecting group having the acyl group CH$_3$(CH$_2$)nCO where n=0–24; and Xaa is Met, Gly, Ser, Phe, Nle, Arg or Glu, and wherein the compound is continuously administered by intravenous infusion at 0.0556 pmol/kg body weight/hour to 5.56 nmol/kg body weight/hour.

2. The method of claim 1 further comprising the step of administering to the subject an intravenous bolus of 4 nmol/kg body weight of PACAP38 before continuously administering the compound.

3. A method of preventing or attenuating neuronal cell death comprising continuously administering to a subject in need thereof a compound selected from the group consisting of:

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-NH$_2$ (SEQ ID NO:3),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-OH (SEQ ID NO:4),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-NH$_2$ (SEQ ID NO:5),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-OH (SEQ ID NO:6),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-NH$_2$ (SEQ ID NO:7),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-OH (SEQ ID NO:8),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-NH$_2$ (SEQ ID NO:9),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-OH (SEQ ID NO:10),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-NH$_2$ (SEQ ID NO:11),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-OH (SEQ ID NO:12),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-NH$_2$ (SEQ ID NO:13),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-OH (SEQ ID NO:14),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-NH$_2$ (SEQ ID NO:15),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-OH (SEQ ID NO:16),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-NH$_2$ (SEQ ID NO:17),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-OH (SEQ ID NO:18),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-NH$_2$ (SEQ ID NO:19),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-OH (SEQ ID NO:20),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-Lys-NH$_2$ (SEQ ID NO:21),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-Lys-OH (SEQ ID NO:22),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-Lys-Asn-NH$_2$ (SEQ ID NO:23),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-Lys-Asn-OH (SEQ ID NO:24),

X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ (SEQ ID NO:25), and X-His-Ser-Asp-Gly-Ile-Phe-Thr-Asp-Ser-Tyr-Ser-Arg-Tyr-Arg-Lys-Gln-Xaa-Ala-Val-Lys-Lys-Tyr-Leu-Ala-Ala-Val-Leu-Gly-Lys-Arg-Tyr-Lys-Gln-Arg-Val-Lys-Asn-Lys-OH (SEQ ID NO:26), wherein:

X is NHR, where R is H or a solubility effecting group having the acyl group $CH_3(CH_2)nCO$ where n=0–24; and Xaa is Met, Gly, Ser, Phe, Nle, Arg or Glu, and wherein the compound is continuously administered by intracerebroventricular infusion at 0.0356 pmol/kg body weight/hour to 35.6 pmol/kg body weight/hour for at least a week.

4. The method of claim 3, wherein the compound is continuously administered at 0.286 pmol/kg body weight/hour to 28.6 pmol/kg body weight/hour.

5. The method of claim 1 or 3, wherein the neuronal cell death is associated with ischemia, reperfusion, trauma, hemorrhage, infection, or exposure to a toxic substance.

6. The method of claim 1 or 3, wherein the neuronal cell death is associated with a neurodegenerative disease.

7. The method of claim 6, wherein the neurodegenerative disease is Parkinson's disease.

8. The method of claim 6, wherein the neurodegenerative disease is Alzheimer's disease.

* * * * *